United States Patent [19]
Choi et al.

[11] Patent Number: 5,820,873
[45] Date of Patent: Oct. 13, 1998

[54] POLYETHYLENE GLYCOL MODIFIED CERAMIDE LIPIDS AND LIPOSOME USES THEREOF

[75] Inventors: Lewis S. L. Choi, Burnaby; Thomas D. Madden; Murray S. Webb, both of Vancouver, all of Canada

[73] Assignee: The University of British Columbia, Vancouver, Canada

[21] Appl. No.: 486,214

[22] Filed: Jun. 7, 1995

Related U.S. Application Data

[63] Continuation-in-part of Ser. No. 316,429, Sep. 30, 1994, abandoned.

[51] Int. Cl.$^6$ .......................... A61K 9/127; A61K 45/00; A61K 39/00; A61K 39/395
[52] U.S. Cl. .................. 424/283.1; 424/450; 424/184.1; 424/812; 424/1.21; 436/529; 436/535; 514/885
[58] Field of Search ................................ 424/283.1, 450, 424/184.1, 885, 1, 417, 812, 1.21; 514/885; 436/529, 535

[56] References Cited

U.S. PATENT DOCUMENTS

| | | | |
|---|---|---|---|
| 4,089,801 | 5/1978 | Schneider | 252/316 |
| 4,460,560 | 7/1984 | Tokes et al. | 424/1.1 |
| 4,501,728 | 2/1985 | Geho et al. | 424/38 |
| 4,534,899 | 8/1985 | Sears | 544/80 |
| 4,544,545 | 10/1985 | Ryan et al. | 424/1.1 |
| 4,617,186 | 10/1986 | Schafer et al. | 424/78 |
| 4,650,909 | 3/1987 | Yoakum | 568/621 |
| 4,728,575 | 3/1988 | Gamble et al. | 428/402.2 |
| 4,737,323 | 4/1988 | Martin et al. | 264/4.3 |
| 4,752,425 | 6/1988 | Martin et al. | 264/4.6 |
| 4,837,028 | 6/1989 | Allen | 424/450 |
| 4,861,521 | 8/1989 | Suzuki et al. | 260/403 |
| 4,920,016 | 4/1990 | Allen et al. | 424/450 |
| 4,925,661 | 5/1990 | Huang | 424/85.91 |
| 4,943,624 | 7/1990 | Regen | 528/301 |
| 4,944,948 | 7/1990 | Uster et al. | 424/450 |
| 4,963,367 | 10/1990 | Ecanow | 424/485 |
| 5,008,109 | 4/1991 | Tin | 424/422 |
| 5,013,556 | 5/1991 | Woodle et al. | 424/450 |
| 5,064,655 | 11/1991 | Uster et al. | 424/450 |
| 5,153,000 | 10/1992 | Chikawa et al. | 424/450 |
| 5,185,154 | 2/1993 | Lasic et al. | 424/450 |
| 5,206,027 | 4/1993 | Kitaguchi | 424/450 |
| 5,213,804 | 5/1993 | Martin et al. | 424/450 |
| 5,225,212 | 7/1993 | Martin et al. | 424/450 |
| 5,288,499 | 2/1994 | Janoff et al. | 424/450 |
| 5,356,633 | 10/1994 | Woodle et al. | 424/450 |
| 5,395,619 | 3/1995 | Zalipsky et al. | 424/450 |
| 5,527,528 | 6/1996 | Allen et al. | 424/178.1 |
| 5,543,152 | 8/1996 | Webb et al. | 424/450 |
| 5,552,155 | 9/1996 | Bailey et al. | 424/450 |
| 5,593,622 | 1/1997 | Yoshioka et al. | 264/4.32 |

FOREIGN PATENT DOCUMENTS

| | | |
|---|---|---|
| 1270197 | 6/1990 | Canada . |
| 2067133 | 4/1991 | Canada . |
| 2067178 | 4/1991 | Canada . |
| 1305054 | 7/1992 | Canada . |
| 0 118 316 | 3/1983 | European Pat. Off. .......... C07F 9/10 |
| 0 072 111 | 10/1985 | European Pat. Off. . |
| 0 220 797 | 5/1987 | European Pat. Off. . |
| 0 370 491 | 5/1990 | European Pat. Off. . |
| 0 422 543 | 4/1991 | European Pat. Off. ....... A61K 9/127 |
| 0 482 860 | 4/1992 | European Pat. Off. ...... C07C 235/08 |
| 526700 | 2/1993 | European Pat. Off. . |
| 546951 | 6/1993 | European Pat. Off. . |
| 572049 | 12/1993 | European Pat. Off. . |
| 0 445 131 | 4/1994 | European Pat. Off. . |
| 0 354 855 | 12/1994 | European Pat. Off. . |
| 0 496 813 | 12/1994 | European Pat. Off. . |
| 0 496 835 | 5/1995 | European Pat. Off. . |
| 2185397 | 7/1987 | United Kingdom . |
| WO 88/04924 | 7/1988 | WIPO . |
| WO 90/04384 | 5/1990 | WIPO . |
| WO 91/05545 | 5/1991 | WIPO . |
| WO 91/05546 | 5/1991 | WIPO . |
| WO 93/19738 | 10/1993 | WIPO . |
| WO 94/07466 | 4/1994 | WIPO . |
| WO 94/21281 | 9/1994 | WIPO . |
| WO 94/22429 | 10/1994 | WIPO . |
| WO 94/26251 | 11/1994 | WIPO . |
| WO 94/27580 | 12/1994 | WIPO . |
| WO 95/31183 | 11/1995 | WIPO . |
| WO 96/34598 | 11/1996 | WIPO . |

OTHER PUBLICATIONS

Blume, et al., "Specific targeting with poly(ethylene glycol)–modified liposomes: coupling of homing devices to the ends of the polymeric chains combines effective target binding with long circulation times," 1993, *Biochimica et Biophysica Acta., 1149*:180–184.

Chonn, et al., "Ganglioside $G_{M1}$ and hydrophilic polymers increase liposome circulation times by inhibiting the association of blood proteins," 1992, *J. Liposome Res., 2(3)*:397–410.

Danishefsky, et al., "Total Synthesis of Zincophorin," 1988, *J. Am. Chem. Soc.*, 1988, 110:4368–4378.

Gregoriadis, et al., "Coupling of ligands to liposomes independently of solute entrapment; observations on the formed vesicles," 1993, *Biochimica et Biophysica Acta., 1147*:185–193.

Huang, et al., "Extravasation and Transcytosis of Liposomes in Kaposi's Sarcoma–Like Dermal Lesions of Transgenic Mice Bearing the HIV Tat Gene," 1993, *American Journal of Pathology, 143(1)*:10–14.

Kiso, et al., "A Convenient Synthesis of Sphingosine and Ceramide from D–Xylose or D–Galactose," 1986, *J. Carbohydrate Chemistry, 5(2)*:335–340.

(List continued on next page.)

*Primary Examiner*—Ponnathapura Achutamurthy
*Assistant Examiner*—Padmashri Ponnaluri
*Attorney, Agent, or Firm*—Townsend and Townsend and Crew LLP

[57] ABSTRACT

The present invention provides a novel class of polyethylene glycol modified ceramide lipids. The lipids can be used to form liposomes optionally containing various biological agents or drugs, such as anti-cancer agents. In addition, methods of use for the liposomes are provided.

30 Claims, 5 Drawing Sheets

OTHER PUBLICATIONS

Klibanov, et al., "Activity of amphipathic poly(ethyleneglycol) 5000 to prolong the circulation time of liposomes depends on the liposome size and is unfavorable for immunoliposome binding to target," 1991, *Biochimica et Biophysica Acta.*, 1062:142–148.

Liu, et al., "Role of liposome size and RES blockade in controlling biodistribution and tumor uptake of $GM_1$–containing liposomes," 1992, *Biochimica et Biophysica Acta.*, 1104:95–101.

Mori, et al., "Influence of the steric barrier activity of amphipathic poly(ethyleneglycol) and ganglioside $GM_1$ on the circulation time of liposomes and on the target binding of immunoliposomes in vivo," 1991, *FEBS Letters*, 284(2):263–266.

Nicolaou, et al., "A Practical and Enantioselective Synthesis of Glycosphingolipids and Related Compounds. Total Synthesis of Globotriaosylceramide ($Gb_3$)," 1988, *J. Am. Chem. Soc.*, 110:7910–7912.

Oikawa, et al., "Selective hydrogenolysis of the benzyl protecting group for hydroxy function with Raney nickel in the presence of the MPM (4–methoxybenzyl) and DMPM (3,4–dimethoxybenzyl) protecting groups," 1984, *Tetrahedron Letters*, 25(47):5397–5400.

Parr, et al., "Factors influencing the retention and chemical stability of poly(ethylene glycol)–lipid conjugates incorporated into large unilamellar vesicles," Jun. 19–22, 1994, Liposome Research Days Conference—Liposomes: The Next Generation, University of British Columbia.

Parr, et al., "Factors influencing the retention and chemical stability of poly(ethylene glycol)–lipid conjugates incorporated into large unilamellar vesicles," 1994, *Biochimica et Biophysica Acta*, 1195:21–30.

Reed, et al., "Generation of targets for alloreactive CTL using purified $H–2K^k$ in liposomes and polyethylene glycol," 1986, *Molecular Immunology*, 23(12):1339–1347.

Schmidt, et al., "Lactosylceramides with Unsaturated Fatty Acids—Synthesis and Use in the Generation of Bilayer Membranes," 1987, *Angew. Chem. Int. Ed. Engl.*, 26(8):793–794.

Torchilin, et al., "Targeted accumulation of polyethylene glycol–coated immunoliposomes in infarcted rabbit myocardium," 1992, *The FASEB Journal*, 6:2716–2719.

Wang, et al., "pH–sensitive immunoliposomes mediate target–cell–specific delivery and controlled expression of a foreign gene in mouse," 1987, *Proc. Natl. Acad. Sci. USA*, 84:7851–7855.

Abuchowski, et al., "Treatment of L5178Y Tumor–Bearing BDF Mice With a Nonimmunogenic L–Glutaminase–L–Asparaginase,"*Cancer Treatment Reports*, 63(6):1127–1132 (1979).

Abuchowski, et al., "Immunosuppressive Properties and Circulating Life of Achromobacter Glutaminase–Asparaginase Covalently Attached to Polyethylene Glycol in Man," *Cancer Treatment Reports*, 65(11–12):1077–1081 (1981).

Berger, Jr., et al., "Preparation of Polyethylene Glycol–Tissue Plasminogen Activator Adducts That Retain Functional Activity: Characteristics and Behavior in Three Animal Species," *Blood*, 71(6):1641–1647 (1988).

Allen, T., *Journal of Liposome Research*, 2(3):289–305 (1992).

Chu, et al., *Journal of Liposome Research*, 4(1):361–395 (1994).

Gao, et al., *Journal of Liposome Research*, 3(1):17–30 (1993).

Klibanov, et al., *Journal of Liposome Research*, 2(3):321–334 (1992).

Soehnlein, et al., *Seifen, Ole, Fette, Wachse*, 115(3):85–86 (1989).

Hyde et al. Nature. vol. 362. 18 Mar. 1993.

POLYETHYLENE GLYCOL MODIFIED CERAMIDE LIPIDS AND LIPOSOME USES THEREOF

CROSS-REFERENCE TO RELATED APPLICATION

This application is a continuation-in-part application of U.S. Ser. No. 08/316,429, filed Sep. 30, 1994, now abandoned, which is hereby incorporated by reference.

BACKGROUND OF THE INVENTION

1. Field of the Invention

The present invention relates to novel polyethylene glycol (PEG) derivatized lipids, their method of preparation and their use in liposomes or other lipid-based carriers. More specifically, the present invention includes PEG-Ceramide lipids and their inclusion in liposomes for use in drug delivery.

2. The Relevant Art

Liposomes are vesicles comprised of concentrically ordered lipid bilayers which encapsulate an aqueous phase. Liposomes form when lipids, molecules which typically comprise a polar head group attached to one or more long chain aliphatic tails, such as phospholipids, are exposed to water. Upon encountering such media the lipids aggregate to form a structure in which only the polar head groups are exposed to the external media to form an external shell inside which the aliphatic tails are sequestered. See, e.g., Lehninger, *PRINCIPLES OF BIOCHEMISTRY* (Worth, 1982). Liposomes can entrap a variety of bioactive or pharmaceutical agents for delivery of these agents to cells and tissues in vivo. See, e.g., U.S. Pat. No. 5,185,154 to Lasic, et al.; European Patent Application No. 526,700 to Tagawa, et al.; and U.S. Pat. No. 5,013,556 to Woodle, et al.

Liposomes can alter the biodistribution and rate of delivery of an encapsulated bioactive agent in a number of ways. For example, drugs encapsulated in liposomes are protected from interactions with serum factors which may chemically degrade the drug. The size of the liposome compared to the free drug also affects its access to certain sites in the body; this property can be advantageous in limiting drug delivery to certain sites. Uptake by the reticuloendothelial system (RES) can be inhibited by including factors on the liposome surface that inhibit protein association with the liposome or liposome interactions with RES cells, for example, by using PEG-lipids with other lipids such as ganglioside $GM_1$. See, Woodle, supra.

A variety of liposome structures can be formed using one or more lipids. Typical classes of liposome structures include small unilamellar vesicles (SUVs), large unilamellar vesicles (LUVs), or multilamellar vesicles (MLVs). The construction of liposomes and their application as delivery systems is described in the art. See, e.g., *LIPOSOMES*, Marc J. Ostro, ed. (Marcel Dekker 1983).

Liposomes have been prepared by derivatizing existing lipid systems to form new liposome structures. For example, polyethyleneglycol (PEG) derivatized lipids have been developed. See Woodle, supra.

Typically, PEG-lipids are prepared by derivatization of the polar head group of a diacylglycerophospholipid, such as distearoylphosphatidylethanolamine (DSPE), with PEG. These phospholipids usually contain two fatty acyl chains bonded to the 1- and 2- position of glycerol by ester linkages. Unfortunately, these acyl groups are susceptible to cleavage under acidic or basic conditions. The resulting hydrolytic products, such as analogs of lysophospholipid and glycerophosphate, do not remain associated with the bilayer structure of the liposome. Such dissociation may weaken the integrity of the liposome structure, leading to significant leakage of the bioactive agent or drug from the liposome and contributing to instability during storage, and thus shortened shelf-life of the liposome product. In addition, the loss of these hydrolysis products, such as PEG-lysophospholipid, from the liposome would negate the benefits otherwise resulting from the presence of the PEG-phospholipid.

Lipid stability is important in the development of liposomal drug delivery systems. This is especially relevant when a transmembrane pH gradient is used to entrap or encapsulate the bioactive agent in the liposome, as very acidic (pH 2–4) or basic (pH 10–12) conditions may be used to achieve efficient drug uptake and retention. Therefore, it is desirable to develop PEG-lipids that are less susceptible to hydrolysis, thereby, increasing the liposome circulation longevity.

SUMMARY OF THE INVENTION

In one aspect, the present invention includes novel PEG-lipids such as the PEG-modified ceramide lipids of Formula I:

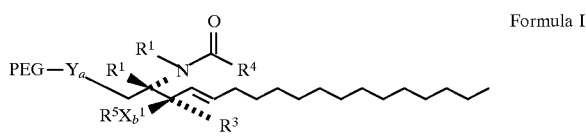

Formula I wherein:

$R^1$, $R^2$, and $R^3$ are independently hydrogen, $C_1$–$C_6$ alkyl, acyl, or aryl;

$R^4$ is hydrogen, $C_1$–$C_{30}$ alkyl, $C_2$–$C_{30}$ alkenyl, $C_2$–$C_{30}$ alkynyl, or aryl;

$R^5$ is hydrogen, alkyl, acyl, aryl, or PEG;

$X^1$ is —O—, —S—, or —$NR^6$—, where $R^6$ is hydrogen, $C_1$–$C_6$ alkyl, acyl or aryl; or when $R^5$ is PEG and b is 1, $X^1$ is also —$Y^1$-alk-$Y^2$—;

Y is —$NR^7$—, where $R^7$ is hydrogen, $C_1$–$C_6$ alkyl, acyl or aryl, or Y is —O—, —S— or —$Y^1$-alk-$Y^2$—, wherein $Y^1$ and $Y^2$ are independently amino, amido, carboxyl, carbamate, carbonyl, carbonate, urea, or phosphoro; and alk is $C_1$–$C_6$ alkylene;

PEG is a polyethylene glycol with an average molecular weight from about 550 to about 8,500 daltons optionally substituted by $C_1$–$C_3$ alkyl, alkoxy, acyl or aryl; wherein a is 0 or 1; and b is 1 unless $R^5$ is PEG wherein b is 0 or 1.

More preferred are those compounds wherein $R^1$, $R^2$, $R^3$, and $R^5$ are hydrogen; $R^4$ is alkyl; $X^1$ is O, Y is succinate; and PEG has an average molecular weight of about 2,000 or about 5,000 daltons and is substituted with methyl at the terminal hydroxyl position.

Also preferred are those compounds wherein $R^1$, $R^2$, $R^3$, and $R^5$ are hydrogen, $R^4$ is alkyl; $X^1$ is O; Y is —NH—; and PEG has an average molecular weight of about 2,000 or about 5,000 daltons and is substituted with methyl at the terminal position.

Other preferred lipid compounds are those wherein $R^1$, $R^2$, $R^3$, and $R^5$ are hydrogen; $R^4$ is $C_7$–$C_{23}$ alkyl, $X^1$ is O; Y is succinate; and PEG has an average molecular weight of about 2,000 daltons and is substituted with methoxy at the terminal hydroxyl position; more preferred are those lipid compounds wherein $R^4$ is $C_{13}$–$C_{19}$ alkyl.

In another aspect, the present invention includes liposomes or other lipid-based carriers including the above-described PEG-Ceramide lipids. Preferred liposome compositions include the preferred lipids described above. In construction of the liposomes, various mixtures of the described PEG-Ceramide lipids can be used in combination and in conjunction with other lipid types, such as DOPE and DODAC, as well as DSPC, SM, Chol and the like, with DOPE and DODAC preferred. Typically, the PEG-Ceramide will comprise about 5 to about 30 mol % of the final liposome construction, but can comprise about 0.0 to about 60 mol % or about 0.5 to about 5 mol %. More preferred lipid compositions are those wherein a drug or a biological agent is encapsulated within the liposome. The invention also includes lipid complexes whereby the PEG-Ceramide lipid comprises about 0.01 to about 90 mol % of the complex.

In still another aspect, the present invention includes methods for delivering therapeutic agents such as drugs and vaccines to a patient in need thereof comprising administering to the patient a therapeutically effective amount of such therapeutic agent in a liposome or a lipid-based carrier of the invention. Also provided are kits for preparing labeled liposomes, containing the PEG-Ceramide lipids, and pharmaceutical formulations containing liposomes.

BRIEF DESCRIPTION OF THE DRAWINGS

FIG. 1A shows plasma clearance of 100 nm liposomes prepared of distearylphosphatidylcholine (DSPC) /Cholesterol (Chol) (55:45 mol %; open circles), DSPC/Chol/PEG$_{2000}$Ceramide (50:45:5 mol %; filled circles), and DSPC/Chol/PEG$_{5000}$Ceramide (50:45:5 mol %; filled squares). FIG. 1B shows plasma clearance of 100 nm liposomes prepared of DSPC/Chol (55:45 mol %; open circles), Sphingomyelin (SM)/Chol (55:45 mol %; filled circles), and Sphingomyelin/Chol/PEG$_{2000}$Ceramide (50:45:5 mol %; open squares).

DETAILED DESCRIPTION OF THE PREFERRED EMBODIMENT

Figure 1A:
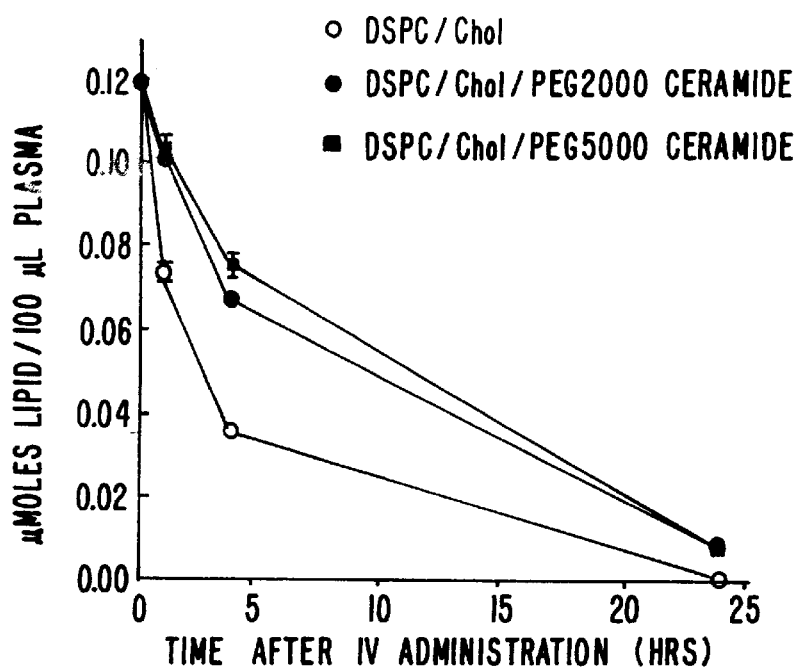
FIG. 1A and FIG. 1B illustrate graphically the circulation lifetimes of the PEG modified ceramide liposomes of the invention.

The PEG-modified ceramide lipids of Formula I enhance the properties of liposomes by increasing the circulation longevity or lifetime of the liposome; preventing aggregation of the liposomes during covalent protein coupling, such as for targeting; preventing aggregation of liposomes incorporating targeting moieties or drugs, such as antibodies, and DNA; promoting drug retention within the liposome; and/or increasing bilayer or other stability of the liposome when low pH is required for encapsulation of the bioactive agents. These PEG-Ceramide lipids also reduce leakage due to hydrolysis of the fatty acyl chains of the liposome bilayer and are more stable than other lipid forms.

DEFINITIONS

As used herein, the term "alkyl" denotes branched or unbranched hydrocarbon chains, such as, e.g., methyl, ethyl, n-propyl, iso-propyl, n-butyl, sec-butyl, iso-butyl, tert-butyl, and 2-methylpentyl. These groups may be optionally substituted with one or more functional groups which are attached commonly to such chains, such as, e.g., hydroxyl, bromo, fluoro, chloro, iodo, mercapto or thio, cyano, alkylthio, heterocycle, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl and cyanobutyl and the like.

The term "alkylene" refers to divalent alkyl as defined above, e.g., methylene (—CH$_2$—), propylene (—CH$_2$CH$_2$CH$_2$—), chloroethylene (—CHClCH$_2$—), 2-thiobutene (—CH$_2$CH(SH)CH$_2$CH$_2$—), 1-bromo-3-hydroxyl-4-methylpentene (—CHBrCH$_2$CH(OH)CH(CH$_3$)CH$_2$—) and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as, e.g., phenyl, naphthyl, indenyl, and the like, and which may be substituted with one or more functional groups which are attached commonly to such chains, such as, e.g., hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl and the like.

The term "acyl" denotes groups —C(O)R, where R is alkyl or aryl as defined above, such as formyl, acetyl, propionyl, or butyryl.

The term "alkoxy" denotes —OR—, wherein R is alkyl.

The term "amido" denotes an amide linkage: —C(O)NH—.

The term "amino" denotes an amine linkage: —NR— wherein R is hydrogen or alkyl.

The term "carboxyl" denotes —C(O)O—, and the term "carbonyl" denotes —C(O)—.

The term "carbonate" indicates —OC(O)O—.

The term "carbamate" denotes —NHC(O)O—, and the term "urea" denotes —NHC(O)NH—.

The term "phosphoro" denotes —OP(O)(OH)O—.

Structure and Preparation of Lipid Compounds

The compounds of the invention are synthesized using standard techniques and reagents. It will be recognized that the compounds of the invention will contain various amide, amine, ether, thio, ester, carbonate, carbamate, urea and phosphoro linkages. Those of skill in the art will recognize that methods and reagents for forming these bonds are well known and readily available. See, e.g., March, *ADVANCED ORGANIC CHEMISTRY* (Wiley 1992), Larock, *COMPREHENSIVE ORGANIC TRANSFORMATIONS* (VCH 1989); and Furniss, *VOGEL'S TEXTBOOK OF PRACTICAL ORGANIC CHEMISTRY* 5th ed. (Longman 1989). It will also be appreciated that any functional groups present may require protection and deprotection at different points in the synthesis of the compounds of the invention. Those of skill in the art will recognize that such techniques are well known. See, e.g., Green and Wuts, *PROTECTIVE GROUPS IN ORGANIC SYNTHESIS* (Wiley 1991).

A general sequence of reactions for forming the compound of the invention is illustrated below in Reaction Scheme I. As shown therein, ceramide derivative 1 is reacted with the PEG derivative PEG-$Y^1$-alk-RG. $R^1$–$R^4$ and $Y^1$ have their meanings as defined above. RG is a group which reacts with $X^2$ to form the desired linkage $Y^2$ between PEG and the ceramide derivative (i.e., —$Y^1$-alk-$Y^2$—). Thus, it will be appreciated that the identities of RG and $X^2$ will be complementary to each other and defined in such a way as to provide the desired linkage. For example, where RG is a nucleophilic center, such as —SH, —OH, or —NH$_2$, $X^2$ may be oxygen derivatized to form a good leaving group, such as —OTs where Ts represents the tosyl group, or halogen. Conversely, $X^2$ may be a nucleophilic center, e.g., —SH, —OH, or —NH$_2$, and RG a group which is reactive toward nucleophilic attack, e.g., carboxyl activated with dicyclohexylcarbodiimide (DCC) or acyl chloride (—COCl). By suitable choice of RG and $X^2$, the desired amido, amine, ether, ester, thioether, carboxyl, carbamate, carbonyl, carbonate, urea or phosphoro coupling between the linker and the ceramide may be obtained. Finally any protecting groups, e.g., $R^8$, remaining on the intermediate 2 are converted to form the desired PEG-Ceramide derivative 3.

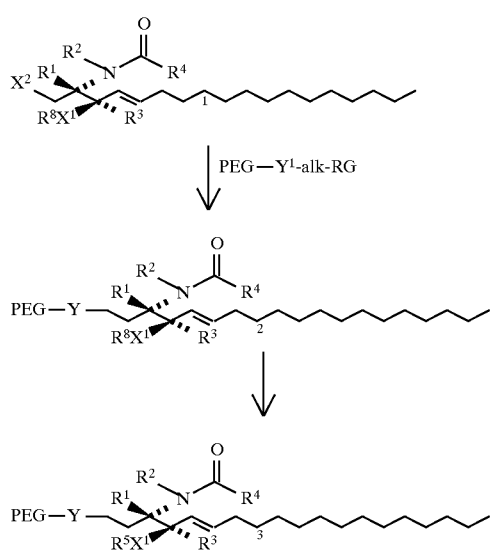

Reaction Scheme I

An exemplary synthesis of the PEG-Ceramide lipids of the invention wherein $Y^1$ and $Y^2$ are carboxyl is illustrated below in Reaction Scheme II. To eliminate the potential problem of crosslinkage formation, PEG is capped at one end by an unreactive group such as methoxy or ethoxy. The second hydroxy group at the other terminal of the PEG molecule is either activated with a suitable reagent such as cyanuric acid, 1,1'-carbonyldiimidazole (CDI) or tresyl halide. Alternatively the terminal hydroxyl group may first be converted to a derivative that can be readily reacted with ceramide in the presence of appropriate condensation reagents, such as the succinate or amine. In other alternative methods, the hydroxy groups on ceramide can be selectively activated for conjugation with PEG, or the two compounds can be linked in a concerted coupling reaction by established coupling procedures.

In the example shown, the primary hydroxyl group of ceramide [available commercially from Sigma Chemical Company (St. Louis, Mo.) and Avanti Polar Lipids Inc. (Alabaster, Ala.)] is reacted with a hydroxyl protecting group of the type which favors reaction at primary alcohols over secondary and tertiary alcohols. Preferred protecting groups are those which are considered sterically hindered, such trityl chloride (TrCl) which comprises three phenyl rings attached to a central carbon atom. However, other protecting groups are known in the art (see, Green and Wuts supra). This reaction is performed using standard techniques and conditions.

Following the protection of the $C_1$ hydroxyl group, the secondary alcohol at $C_3$ is protected with a second protecting group. The second protecting group should be one which is reactive towards more hindered secondary alcohols, but which is not removed under conditions effective to remove the protecting group blocking the $C_1$ alcohol. A preferred protecting group is benzyl (Bn). Again, other suitable protecting group combinations will be apparent to those of skill in the art.

Once both of the hydroxyl groups are protected, the $C_1$—OH protecting group is removed under conditions which do not affect the protecting group at the $C_3$ alcohol. The free hydroxyl function is then reacted with the PEG derivative Me(PEG)OC(O)CH$_2$CH$_2$CO$_2$H with dicyclohexylcarbodiimide (DCC) and 4-N,N'-dimethylaminopyridine (DMAP) to form the desired PEG-Ceramide derivative.

The protecting group at $C_3$ can be removed, if desired, to permit other reactions at this site to obtain other substituent groups.

amido —C(O)NH—. As shown in the scheme, the 1-amino analog of ceramide can be prepared by derivitization of the $C_1$ hydroxyl group first to the corresponding $C_1$ alkyl sulfonate (e.g., methyl sulfonate or 2,2,2-trifluoroethanesulfonate). The latter is converted to the amino analog directly with ammonia or through an azide intermediate as shown. The 1-amino-ceramide is then coupled to the N-hydroxysuccinamide (NHS) ester of MePEG-S to form a MePEG-S-ceramide with an amide linkage.

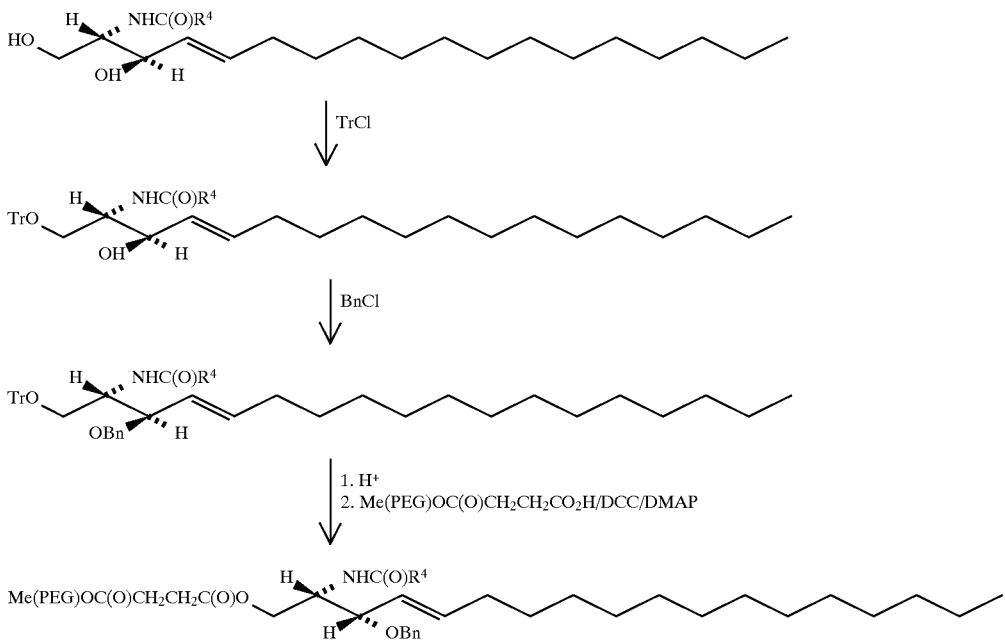

In another approach, shown in Reaction Scheme III below, $Y^1$ is a carboxyl ester group —OC(O)— and $Y^2$ is an

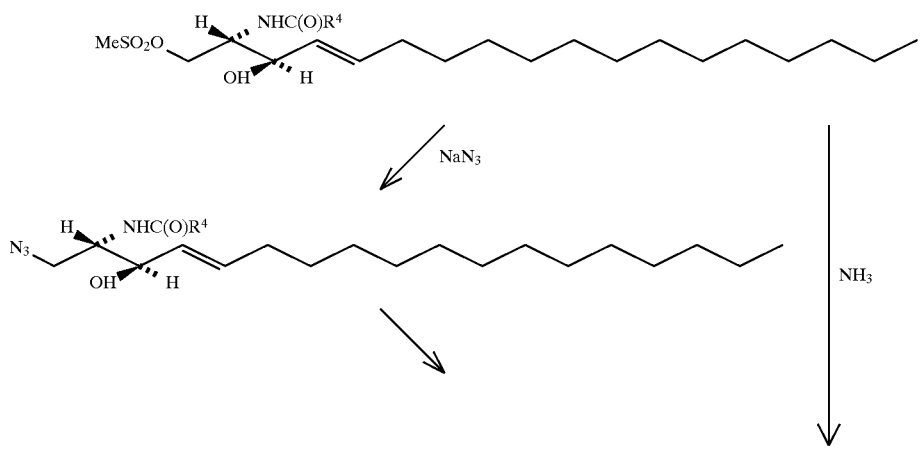

-continued
Reaction Scheme III

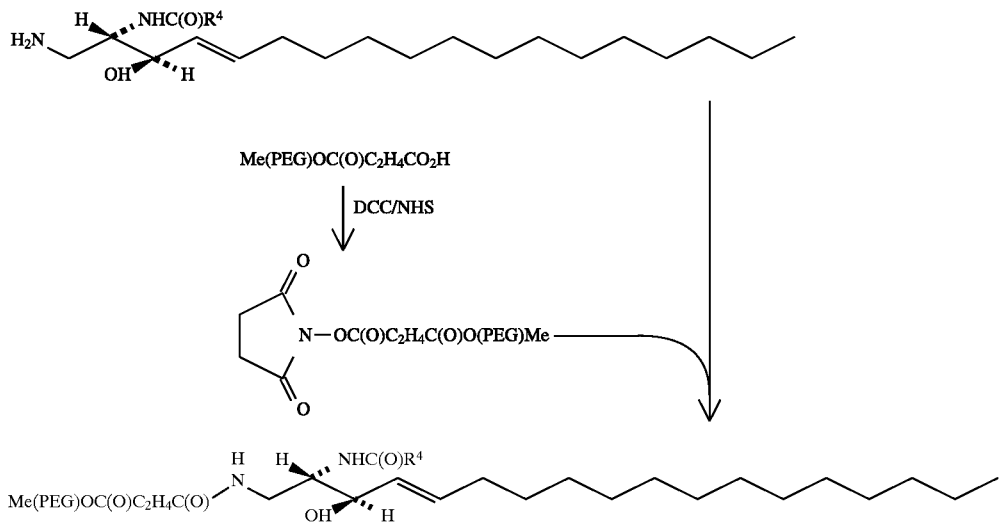

Alternatively, the group Y may be —NR⁷—, where $R^7$ is hydrogen, alkyl, acyl, or aryl; or Y may be —O— or —S—. Such embodiments may be formed using well known methods and reagents. For example, the embodiment wherein Y is —NH— can be made by the synthesis pathway shown in Reaction Scheme IV below. There, the 1-mesyl-ceramide described above is reacted with the amino analog of (MePEG-NH₂) to form the desired MePEG-Ceramide conjugate having an amino linkage.

Reaction Scheme IV

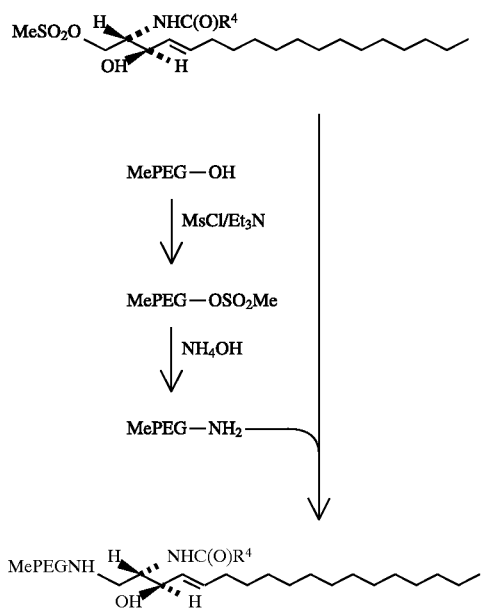

Both the $C_1$ and $C_3$ hydroxy functions in ceramide can be activated with a reagent such as CDI to form the corresponding bis-imidazolyl formate. The latter is then reacted with the amino group of MePEG-NH₂ to form a conjugate with two MePEG molecules bonded to one ceramide. Either one or two PEG molecules can be selected to attach to each ceramide, allowing a more flexible arrangement for introducing specific properties to a liposomal system.

The group $Y=Y^1$-alk-$Y^2$ can be formed from readily available starting materials using known techniques. Preferred embodiments include those wherein $Y^1$ and $Y^2$ are both carbonyl (—C(O)—) or where one of $Y^1$ or $Y^2$ is carbonyl and the other is amido (—C(O)NH—). These groups can be formed from commercially available diacids, such as malonic acid ($CH_2(CO_2H)_2$), succinic acid ($HO_2CCH_2CH_2CO_2H$), glutaric acid ($HO_2CCH_2CH_2CH_2CO_2H$) and adipic acid ($HO_2CCH_2CH_2CH_2CH_2CO_2H$) and the like; as well as substituted diacids, such as tartaric acid ($HO_2CCH(OH)CH(OH)CO_2H$), 3-methylglutaric acid ($HO_2CCH_2CH(CH_3)CH_2CO_2H$) and the like, using methods well known in the chemical arts. Acyl derivatives, such as acyl chlorides, e.g., 3-carbomethoxypropiponyl chloride (ClC(O)$C_2H_4CO_2CH_3$), and amides corresponding to these compounds are available commercially or can be formed using known procedures.

PEG is a linear, water-soluble polymer of ethylene oxide repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include:

monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH₂), monomethoxypolyethylene glycol-tresylate (MePEG-TRES), and monomethoxypolyethylene glycol-imidazolyl-carbonyl (MePEG-IM).

The attachment of PEG to the linker Y may be performed using methods and materials known in the art. Generally, a hydroxyl or amino moiety of the PEG group, is reacted with suitable derivative of Y so as to form the desired coupling. For example, reaction of a free hydroxyl functionality of MePEG-OH with an acyl chloride derivative, such as 3-carbomethoxypropiponyl chloride (ClC(O)$C_2H_4CO_2CH_3$), available commercially from Aldrich Chemical Co., Milwaukee, Wis., provides Me(PEG)-OC(O)$C_2H_4CO_2CH_3$. The methyl ester can be further derivatized, e.g., to the acyl chloride or amide, using standard procedures. Alternatively, Me(PEG)OC(O)CH$_2$CH$_2$CO$_2$H may be formed from Me(PEG)-OH and succinic anhydride as shown below:

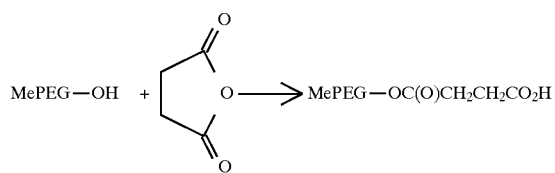

Still other methods will be apparent to those of skill in the art.

To couple PEG directly to the ceramide, the hydroxy function in MePEG can be directly activated with reagent such as CDI to form the corresponding imidazolyl formate. The latter is then reacted with a nucleophile, such as one or both alcohol functions of ceramide, to form a conjugate with a carbonate linkage. Alternatively, coupling of the MePEG imidazolyl formate with 1-aminoceramide will result in the formation of a MePEG-Ceramide adduct with a carbamate linkage.

Commercial ceramides, which are N-acyl fatty acids of sphingosines, may be obtained by phospholipase C cleavage of the phosphocholine in the respective sphingomyelin precursors, which are extracted from egg yolks and brain tissue. The sphingomyelin lipids differ in the composition of the fatty amide chains, such as in the carbon chain length and the number of double bonds. The following ceramides are commercially available from Sigma Chemical Co. and Avanti Polar Lipids Inc.: (1) Type III: from bovine brain (approximately 99%); (2) Type IV: bovin brain (approximately 99%); (3) from brain (approximately 99%); and (4) from egg (approximately 99%). The fatty amide chains differ in composition based upon the source of the sphingomyelin, as shown in Table I:

TABLE I

FATTY ACID CONTENT OF TISSUE DERIVED SPHINGOMYELIN

| Fatty Acid | Egg Sphingomyelin | Brain Sphingomyelin |
|---|---|---|
| 16:0 | 77.70 | 2.38 |
| 18:0 | 7.44 | 57.99 |
| 20:0 | 1.83 | 6.08 |
| 22:0 | 3.98 | 9.16 |
| 24:0 | 1.86 | 7.04 |
| 24:1 | 2.80 | 14.71 |

A wide variety of ceramide derivatives may be synthesized from common starting materials using known techniques. For example, starting from commercially available erythritol (Aldrich, Milwaukee, Wis.), any ceramide derivative may be synthesized as illustrated in Reaction Scheme V below. Selective protection of erythritol using known methods provides the starting material shown in Reaction Scheme V, wherein the C$_1$ and C$_3$ carbons are protected as the benzyl (Bn) derivatives, the C$_2$ carbon is protected as the methylmethoxy (MOM) ether and the C$_4$ carbon is protected as the 3,4-dimethoxybenzyl (DMPM) ether derivative. Selective removal of the DMPM group using dichlorodicyanoquinone (DDQ) provides the corresponding alcohol which can be oxidized using standard methods to form the aldehyde as shown (see, e.g., Larock, supra).

Reaction of the aldehyde with the Wittig reagent Et$_3$P$^+$C$_{14}$H$_{29}$Br$^-$ provides the trans olefin preferentially. Alternatively, reaction with the triphenylphosphine derivative Ph$_3$P$^+$C$_{14}$H$_{29}$Br$^-$ provides the cis olefin predominantly. Again, other methods of olefin formation will be apparent to those of skill in the art. Removal of the MOM protecting group, followed by conversion of the alcohol using sodium azide (NaN$_3$) and lithium aluminum hydride (LiAlH$_4$) provides the desired amine which is reacted with an acyl chloride to produce the amide shown. Reaction of the amide with boron trichloride (BCl$_3$) in methylene chloride (CH$_2$Cl$_2$) using a temperature gradient from −78° C. to 0° C., followed by reaction with methanol (MeOH) at −78° C., provides the desired diol. Other equivalent methods of synthesis will be apparent to those of skill in the art. Additional information regarding the synthesis of sphingolipids and optically active ceramides can be found in Schmidt, et al. *ANGEW. CHEM. INT.* Ed. Engl (1987) 26:793; Kiso, et al. *J. CARBOHYDR. CHEM.* (1986) 5:335; and Nicolaou, et al. *J. AMER. CHEM. SOC.* (1988) 110:7910.

Ceramides of varying fatty amide chain lengths also can be prepared by reacting the amine of Scheme V with various acyl chlorides [R$^4$C(O)Cl] or other acyl or acid derivatives, whereby the carbon chain length is based upon the particular acyl group used. Typically and preferably, the carbon chain length is from about 8 to about 24, without any double bonds present, e.g., an alkyl chain. Most preferred are those ceramides designated as 20:0, which designates a 20 carbon length chain with no double bonds, i.e., a completely saturated C$_{20}$ alkyl as the fatty amide chain. Alternatively, ceramides with specific acyl chains of homogenous composition can be prepared by conjugation of a suitably activated carboxylic compounds, such as N-hydroxysuccinimide (NHS) ester of fatty acid, with the amino function of D-sphingosine. For example, an acyl chloride of eicosanoic acid (also known as arachidic acid) will provide a chain 20 carbons (C20) in length for the resulting amide side chain. Other acids preferably include: octanoic acid (also known as caprylic acid) for C8; myristic acid for C14; palmitic acid (also known as hexadecanoic acid) for C16; and tetracosanoic acid (also known as lignoceric acid) for C24. Ceramides with fatty amide chain lengths of 14 to 20 carbons are especially preferred. Most preferred are those 14 or 20 carbons in length. (It is understood that R4 is one carbon shorter in length than the starting acyl chloride or acid.)

Reaction Scheme V

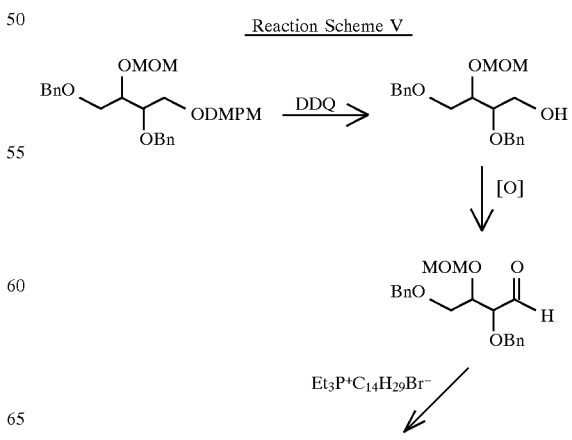

-continued
Reaction Scheme V

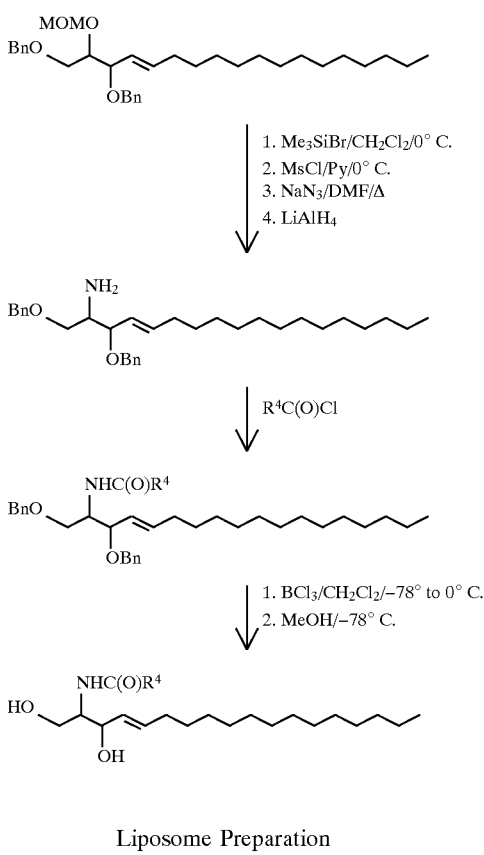

Liposome Preparation

After the lipids of Formula I are prepared, they can be utilized in liposome structures incorporating or entrapping one or more bioactive agents, wherein one or more of the lipid compounds comprise the liposome. For example, the fatty amide chain can have various lengths on the ceramide portion of the lipid, and a mixture of the various resulting lipid compounds forms the desired liposome. In addition, non-PEG ceramide lipids can be used to construct the liposome in conjunction with the lipids of Formula I.

A variety of methods are available for preparing liposomes as described in, e.g., Szoka et al., 9 ANN. REV. BIOPHYS. BIOENG. 467 (1980); U.S. Pat. Nos. 4,235,871, 4,501,728, 4,837,028; the text LIPOSOMES Ch. 1 (supra) and Hope et al., 40 CHEM. PHYS. LIP. 89 (1986). One method produces multilamellar vesicles of heterogeneous sizes. In this method, the vesicle-forming lipids are dissolved in a suitable organic solvent or solvent system and dried under vacuum or an inert gas to form a thin lipid film. Alternatively, the lipids may be dissolved in an organic solvent such as tert-butyl alcohol or benzene:methanol (95:5 v/v) and lyophilized to form a homogeneous lipid mixture, which is in a more easily hydrated powder-like form. The dry lipid mixture is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions. Full hydration of the lipids may be enhanced by freezing in liquid nitrogen and thawing to about 50° C. This cycle is usually repeated about five times.

Following liposome preparation, the liposomes may be sized to achieve a desired size range and relatively narrow distribution of liposome sizes. A size range of about 0.05–0.20 microns allows the liposome suspension to be sterilized by filtration through a conventional filter, using typically a 0.22 micron filter. The filter sterilization method can be carried out on a high through-put basis if the liposomes have been sized down to about 0.05–0.20 microns.

Several techniques are available for sizing liposomes, such as the sizing method described in U.S. Pat. No. 4,737,323. For example, sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.01 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposomes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of from about 0.05 microns to about 0.20 microns are preferred. Liposome preparations are also described by Deamer et al., in Liposomes (supra) LIPOSOME PREPARATIONS: METHODS AND MECHANISMS.

Liposome size distributions also may be determined by quasi-elastic light scattering techniques. See Bloomfield, 10 Ann. Rev. Biophys. Bioeng. 421 (1981).

Use of Liposomes as Delivery Vehicles

The liposomes prepared by using the lipid compounds of this invention can be labeled with markers that will facilitate diagnostic imaging of various disease states including tumors, inflamed joints or lesions. Typically, these labels will be radioactive markers, although fluorescent labels can also be used. The use of gamma-emitting radioisotopes is particularly advantageous as they easily can be counted in a scintillation well counter, do not require tissue homogenization prior to counting, and can be imaged with gamma cameras.

Gamma- or positron- emitting radioisotopes are typically used, such as $^{99}$Tc, $^{24}$Na, $^{51}$Cr, $^{59}$Fe, $^{67}$Ga, $^{86}$Rb, $^{111}$In, $^{125}$I, and $^{195}$Pt as gamma-emitting; and such as $^{68}$Ga, $^{82}$Rb, $^{22}$Na, $^{75}$Br, $^{122}$I and $^{18}$F as positron-emitting.

The liposomes also can be labelled with a paramagnetic isotope for purposes of in vivo diagnosis, as through the use of magnetic resonance imaging (MRI) or electron spin resonance (ESR). See, for example, U.S. Pat. No. 4,728,575.

Liposomes are a valuable system for the controlled delivery of drugs. As discussed earlier, liposomes formulated from PEG-lipids are especially advantageous, since they are more stable and have an increased half-life in circulation over conventional liposomes. Using liposomes as drug carriers allows more control of the site or rate of release of the drug, enabling more precision to be obtained in regulating the blood and organ levels of drug and/or its metabolites. Thus, drug dosages needed to produce clinical effects can be reduced which in turn reduces toxicity. Toxicity concerns are particularly valid in cancer chemotherapy where the dose levels required for beneficial effects and the doses that result in significant toxicity are very close. Thus, for cancer chemotherapy the use of liposome carriers for antitumor drugs can provide significant therapeutic advantages.

Depending on the capture volume within the liposome and the chemical and physical properties of the bioactive agents, compatible bioactive agents can be simultaneously encapsulated in a single liposome. Simultaneous delivery of two or more synergistic drugs in this manner will ensure the delivery of these drugs to the same location in the body and maintain the drugs in close proximity to act together, thus greatly facilitating therapy.

A wide variety of bioactive agents, pharmaceutical substances, or drugs can be encapsulated within the interior of the relatively impermeable bilayer membranes of the liposomes where these substances can be protected from the environment during transit to their target areas. These substances include antitumor agents, antibiotics, immunomodulators, anti-inflammatory drugs and drugs acting on the central nervous system (CNS). Especially preferred antitumor agents include actinomycin D, vincristine, vinblastine, cystine arabinoside, anthracyclines, alkylative agents, platinum compounds, antimetabolites, and nucleoside analogs, such as methotrexate and purine and pyrimidine analogs. Considering the preferred uptake of intravenously injected liposomes by the bone marrow, lymphoid organs, liver, spleen and lungs, and the macrophage cell, neoplasms and other diseases involving these organs can be effectively treated by PEG-derived liposome-entrapped drug. (See Daoud et al., "Liposomes In Cancer Therapy", 3 ADV DRUG DELIVERY REVIEWS 405–418, 1989.)

Another clinical application of liposomes is as an adjuvant for immunization of both animals and humans. Protein antigens such as diphtheria toxoid, cholera toxin, parasitic antigens, viral antigens, immunoglobulins, enzymes, histocompatibility antigens can be incorporated into or attached onto the liposomes for immunization purposes.

Liposomes are also particularly useful as carriers for vaccines that will targeted to the appropriate lymphoid organs to stimulate an immune response.

Liposomes have been used as a vector to deliver immunosuppressive or immunostimulatory agents selectively to macrophages. In particular, glucocorticoids useful to suppress macrophage activity and lymphokines that activate macrophages have been delivered in liposomes.

Liposomes with targeting molecules can be used to stimulate or suppress a cell. For example, liposomes incorporating a particular antigen can be employed to stimulate the B cell population displaying surface antibody that specifically binds that antigen. Similarly, PEG-stabilized liposomes incorporating growth factors or lymphokines on the liposome surface can be directed to stimulate cells expressing the appropriate receptors for these factors. Such an approach can be used for example, in stimulating bone marrow cells to proliferate as part of the treatment of cancer patients following radiation or chemotherapy which destroys stem cells and actively dividing cells.

Liposome-encapsulated antibodies can be used to treat drug overdoses. The tendency of liposomes having encapsulated antibodies to be delivered to the liver has a therapeutic advantage in clearing substances such as toxic agents from the blood circulation. It has been demonstrated that whereas unencapsulated antibodies to digoxin caused intravascular retention of the drug, encapsulated antibodies caused increased splenic and hepatic uptake and an increased excretion rate of digoxin.

Liposomes comprising PEG-lipids also find utility as carriers in introducing lipid or protein antigens into the plasma membrane of cells that lack the antigens. For example, histocompatibility antigens or viral antigens can be introduced into the surface of viral infected or tumor cells to promote recognition and killing of these cells by the immune system.

In certain embodiments, it is desirable to target the liposomes of the invention using targeting moieties that are specific to a cell type or tissue. Targeting of liposomes using a variety of targeting moieties, such as ligands, cell-surface receptors, glycoproteins, and monoclonal antibodies, has been previously described. See U.S. Pat. Nos. 4,957,773 and 4,603,044. The targeting moieties can comprise the entire protein or fragments thereof.

Targeting mechanisms generally require that the targeting agents be positioned on the surface of the liposome in such a manner that the target moiety is available for interaction with the target; for example, a cell surface receptor. The liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposome's surface and is configured to correctly position the targeting agent. In some cases it is possible to attach the target agent directly to the connector portion, but in many instances, it is more suitable to use a third molecule to act as a "molecular bridge." The bridge links the connector portion and the target agent off of the surface of the liposome, making the target agent freely available for interaction with the cellular target.

Standard methods for coupling the target agents can be used. For example, phosphatidylethanolamine, which can be activated for attachment of target agents, or of derivatized lipophilic compounds, such as lipid-derivatized bleomycin, can be used. Antibody-targeted liposomes can be constructed using, for instance, liposomes that incorporate protein A. See Renneisen et al., 265 J. Biol. Chem. 16337–16342 (1990) and Leonetti et al., 87 Proc. Natl. Acad. Sci. (USA) 2448–2451 (1990). Other examples of antibody conjugation are disclosed in U.S. patent application Ser. No. 08/316,394, filed Sep. 30, 1994, now abandoned, the teachings of which are incorporated herein by reference. Examples of targeting moieties also can include other proteins, specific to cellular components, including antigens associated with neoplasms or tumors. Proteins used as targeting moieties can be attached to the liposomes via covalent bonds. See Heath, Covalent Attachment of Proteins to Liposomes, 149 Methods in Enzymology 111–119 (Academic Press, Inc. 1987). Other targeting methods include the biotin-avidin system.

In some cases, the diagnostic targeting of the liposome can subsequently be used to treat the targeted cell or tissue. For example, when a toxin is coupled to a targeted liposome, the toxin can then be effective in destroying the targeted cell, such as a neoplasmic cell.

Once the encapsulated bioactive agents or the liposomes themselves are taken up by the cell, the bioactive agents also can be targeted to a specific intracellular site of action if target recognizing moieties are incorporated into the agent. For example, protein agents to be delivered to the nucleus may comprise a nuclear localization signal sequence recombinantly engineered into the protein or the signal sequence may be on a separate protein or peptide covalently attached to the primary protein. Likewise, non-protein drugs destined for the nucleus may have such a signal moiety covalently attached. Other target recognizing moieties that can be recombinantly engineered into or covalently attached to protein components to be delivered by liposomes include ligands, receptors and antibodies or fragments thereof.

The present invention also provides a kit for preparing labeled liposomes. The kit will typically be comprised of a container that is compartmentalized for holding the various elements of the kit. One compartment can contain the materials for preparing the label just prior to use. A second compartment can contain the liposomes with or without a pH buffer to adjust the composition pH to physiological range of about 7 to about 8. The liposomes also can be provided in freeze-dried form for reconstitution at the time of use. Also included within the kit will be other reagents and instructions for use.

Liposomes comprising the lipid compounds of this invention can be formulated as pharmaceutical compositions or formulations according to standard techniques using acceptable adjuvants or carriers. Preferably, the physiologically pharmaceutical compositions are administered parenterally, i.e., intravenously, subcutaneously, or intramuscularly. Suitable formulations for use in the present invention are found in REMINGTON'S PHARMACEUTICAL SCIENCES (Mack Publishing Co., 18th ed. 1990).

Preferably, the compositions are administered intravenously. Therefore, this invention provides for compositions for intravenous administration which comprise a solution of liposomes suspended in a physiologically-acceptable adjuvant or carrier, preferably an aqueous carrier, such as water, buffered water, isotonic saline, and the like. The compositions may be sterilized by conventional, well-known sterilization techniques, or may be sterile filtered. The resulting aqueous solutions may be packaged for use as is, or lyophilized; the lyophilized preparation being combined with a sterile aqueous solution prior to administration. The compositions can contain pharmaceutically-acceptable auxiliary substances as required to approximate the appropriate physiological conditions, such as pH adjusting and buffering agents, tonicity adjusting agents, wetting agents, and the like. Such agents include sodium acetate, sodium lactate, sodium chloride, potassium chloride, calcium chloride, sorbitan monolaurate, triethanolamine oleate, and the like.

The concentration of liposomes useful in pharmaceutical compositions can range from about 0.05%, usually about 2–5%, or as much as about 10–30% by weight of the composition and the range of concentration is selected in accordance with the mode of administration and bioactive agent contained within the liposomes.

Since the present liposomes made from PEG-Ceramide lipids are less susceptible to hydrolysis, they have a prolonged half-life resulting in prolonged circulation. Additionally, the liposome pharmaceutical composition can include lipid-protective agents that protect the liposomes against free-radical and lipid-peroxidative damage upon storage. Such protective agents include alpha-tocopherol and water-soluble, iron-specific chelators, such as ferrioxamine.

Use of Lipids or Lipid-Based Carriers as Delivery Vehicles

Cationic lipids may be used in the delivery of therapeutic genes or oligonucleotides intended to induce or to block production of some protein within the cell. Nucleic acid is negatively charged and must be combined with a positively charged entity to form a lipid complex suitable for formulation and cellular delivery.

Cationic lipids have been used in the transfection of cells in vitro and in vivo (Wang C-Y, Huang L. *pH-sensitive immunoliposomes mediate target cell-specific delivery and controlled expression of a foreign gene in mouse. PROC. NATL. ACAD. SCI USA,* 1987; 84:7851–7855 and Hyde S. C., Gill D. R. Higgins C. F., et al. *Correction of the ion transport defect in cystic fibrosis transgenic mice by gene therapy. NATURE.* 1993;362:250–255.) The efficiency of this transfection has often been less than desired, for various reasons. One is the tendency for cationic lipids complexed to nucleic acid to form unsatisfactory carriers. These carriers are improved by the inclusion of PEG lipids.

Cationic lipids useful in producing lipid-based carriers for gene and oligonucleotide delivery are *LIPOFECTIN* (U.S. Pat. Nos. 4,897,355; 4,946,787; and 5,208,036 by Eppstein et al.) and *LIPOFECTACE* (U.S. Pat. No. 5,279,883 by Rose). Both agents, as well as other transfecting cationic lipids, are available from Life Technologies, Inc. in Gaithersburg, Md.

The invention will be better understood by reference to the following examples, which are intended to illustrate aspects of the invention, but the invention is not to be considered as limited thereto.

EXAMPLE 1

N-Eicosanoyl-D-Sphingosine [C20:0-Ceramide]

N-Hydroxysuccinimide (NHS) ester of eicosanoic acid was synthesized using the procedure of Lapidot et al. (*J. Lipid Res.,* 1967, 8:142). 428 mg of the ester was added to a solution of D-sphingosine (Avanti Polar Lipids, Inc.) (300 mg) in anhydrous methylene chloride ($CH_2Cl_2$, 16 ml) and triethylamine (118 mg) with stirring under nitrogen ($N_2$) at 20° C. for 4 hours. Analysis by thin layer chromatography (t.l.c.) (silica gel, $CHCl_3$:$CH_3OH$:$H_2O$—65:25:4 v/v or $CHCl_3$:$CH_3OH$—90:10 v/v) indicated most of the D-sphingosine had reacted. [If necessary, another small portion of NHS-ester of eicosanoic acid (20–30 mg) may be added to complete the acylation of D-sphingosine]. The reaction mixture was cooled in ice and diluted with $CH_2Cl_2$ (60 ml), $H_2O$ (30 ml) and neutralized with 1N HCl. The $CH_2Cl_2$ layer was washed with $H_2O$ (2×30 ml) and dried ($MgSO_4$) before evaporation to dryness in vacuo. The residue was recrystallized twice from acetone to give the pure product, N-eicosanoyl-D-sphingosine (428 mg), as a white solid. T.l.c. showed a single spot and $^1$H-NMR spectrum was consistent with the expected structure.

EXAMPLE 2

Monomethoxypolyethylene Glycol$_{2000}$-Succinate (MePEG$_{2000}$-S)

Monomethoxypolyethylene glycol with an average molecular weight of 2000 daltons (MePEG$_{2000}$) (Sigma Chemical Co.), (4 g) dissolved in $CH_2Cl_2$ (30 ml) was treated with succinic anhydride (600 mg), triethylamine (400 mg) and 4-dimethylaminopyridine (DMAP) (250 mg), and stirred under $N_2$ at 20° C. for 16 hours. The reaction solution was diluted with $CH_2Cl_2$ (60 ml), cooled in ice and $H_2O$ (50 ml) added. The mixture was acidified with 1N HCl and the organic layer separated. The aqueous layer was further extracted with $CH_2Cl_2$ (2×30 ml). The combined organic extracts were dried ($MgSO_4$) and then evaporated to dryness. The crude product was purified on a silica gel (G60) column eluted with a solvent system of $CH_2Cl_2$ containing 2 to 8% methanol. Fractions collected were analyzed by t.l.c. (silica gel, $CHCl_3$:$CH_3OH$-88:12 v/v) and those containing the pure product ($MePEG_{2000}$-S) with $R_f$ value of 0.4 were pooled and concentrated. Trituration of the product with diethyl ether gave $MePEG_{2000}$-S as a white solid (3.2 g).

EXAMPLE 3

Monomethoxypolyethylene Glycol$_{5000}$-Succinate ($MePEG_{5000}$-S)

The titled compound was prepared from monomethoxypolyethylene glycol with an average molecular weight of 5000 daltons ($MePEG_{5000}$) (Sigma Chemical Co.) in a similar procedure as described above for $MePEG_{2000}$-S.

EXAMPLE 4

1-O-($MePEG_{2000}$-S)-(C20: 0-Ceramide)

C20:0-Ceramide (60 mg), dicyclohexylcarbodiimide (DCC) (28 mg) and DMAP (13 mg) were dissolved in warm anhydrous $CH_2Cl_2$ (6 ml). $MePEG_{2000}$-S (230 mg) in anhydrous $CH_2Cl_2$ (1 ml) was added dropwise to the above solution with stirring under $N_2$ at 25° C. for 6 hours. The precipitated dicyclohexylurea (DCU) was filtered off and the filtrate concentrated in vacuo. Trituration of the solid residue with diethyl ether removed most of the DCC, DMAP and unreacted C20:0-ceramide. The resulting crude product was chromatographed on a short silica gel column (G60) eluted with $CH_2Cl_2$:$CH_3OH$-98:2 (v/v). Fractions containing the product were combined and evaporated to dryness in vacuo. The resulting solid was dissolved in distilled $H_2O$ (2 ml) and dialysed at 4° C. against distilled water overnight. The pure product was obtained as a white powder (160 mg) by lyophilization. T.l.c. (silica gel, $CHCl_3$:$CH_3OH$-90:10 v/v showed a single spot ($R_f$ 0.5). $^1H$-NMR spectrum of the product was consistent with the structure of 1-O-($MePEG_{2000}$-S)-(C20:0-ceramide). [$PEG_{2000}$ Ceramide]

EXAMPLE 5

1-O-($MePEG_{2000}$-S) -(Egg Ceramide) [$PEG_{2000}$ Ceramide]

Egg ceramide (Avanti Polar Lipids, Inc.) (108 mg), DCC (48 mg), and DMAP (25 mg) were dissolved in warm anhydrous $CH_2Cl_2$ (8 ml). $MePEG_{2000}$-S (460 mg) in anhydrous $CH_2Cl_2$ (2 ml) was added dropwise to the above solution with stirring under $N_2$ at 25° C. for 6 hours. The precipitated DCU was filtered off and the filtrate concentrated in vacuo. Trituration of the solid residue with diethyl ether removed most of the residual reagents and small amount of unreacted egg ceramide. The crude product was chromatographed on a short silica gel column (G60) eluted with $CH_2Cl_2$:$CH_3OH$-98:2 (v/v). Fractions containing the product were combined and evaporated to dryness in vacuo. The resulting solid was dissolved in distilled water (2 ml) and dialysed at 4° C. against distilled water overnight. Lyophilization of the solution gave the pure product as a white powder (338 mg). T.l.c. (silica gel, $CHCl_3$.OH-90:10 v/v) showed a single spot ($R_f$ 0.5) $^1H$-NMR spectrum of the product was in agreement with the structure of 1-O-($MePEG_{2000}$-S)-(egg ceramide).

EXAMPLE 6

1-O-($MePEG_{5000}$-S)-(egg Ceramide) [$PEG_{5000}$ Ceramide]

The titled compound was prepared from $MePEG_{5000}$-S (550 mg) and egg ceramide (54 mg) in a procedure similar to that described above for 1-O-($MePEG_{2000}$-S)-(egg ceramide) using DCC (28 mg) and DMAP (13 mg) as the condensation reagents in anhydrous $CH_2Cl_2$ (6 ml). Similar purification by column chromatography (silica gel) and dialysis gave the pure product 1-O-($MePEG_{5000}$-S)-(egg ceramide) as a white powder (310 mg).

EXAMPLE 7

Plasma Clearance of Specific Liposomes

In this example, the plasma clearance for 100 nm liposomes prepared of Distearylphosphatidylcholine (DSPC)/ Cholesterol (Chol) (55:45 mol %; open circles); DSPC/ Chol/$PEG_{2000}$Ceramide (50:45:5 mol %; filled circles), and DSPC/Chol/$PEG_{5000}$Ceramide (50:45:5 mol %; filled squares) was determined. The results are shown in FIG. 1A. Lipid mixtures were prepared in chloroform ($CHCl_3$) and subsequently dried under a stream of nitrogen gas. The resulting lipid film was placed under high vacuum for at least 2 hours prior to hydration with 150 mM sodium chloride and 20 mM Hepes (pH 7.4) (Hepes buffered saline solution). Liposomes were then prepared by extrusion through 100 nm pore size filters using an Extruder preheated to 65° C. prior to extrusion. The resulting liposomes exhibited a mean diameter of approximately 120 nm. These liposomes were diluted such that mice (female CD1) could be given an i.v. dose of lipid equivalent to 50 μmoles/kg in an injection volume of 200 μl. At various time points indicated in FIG. 1A, blood samples were taken by nicking the tail vein and collecting 25 μl of blood into a EDTA (ethylenediaminetetraacetic acid) coated capillary tube. The amount of lipid in the resulting sample was determined by measuring the amount of 3[H]-cholesteryl hexadecyl ether present. This non-exchangeable, non-metabolizable lipid marker was incorporated into the liposomes prior to formation of the lipid film.

EXAMPLE 8

Plasma Clearance of Specific Liposomes

Figure 1B:
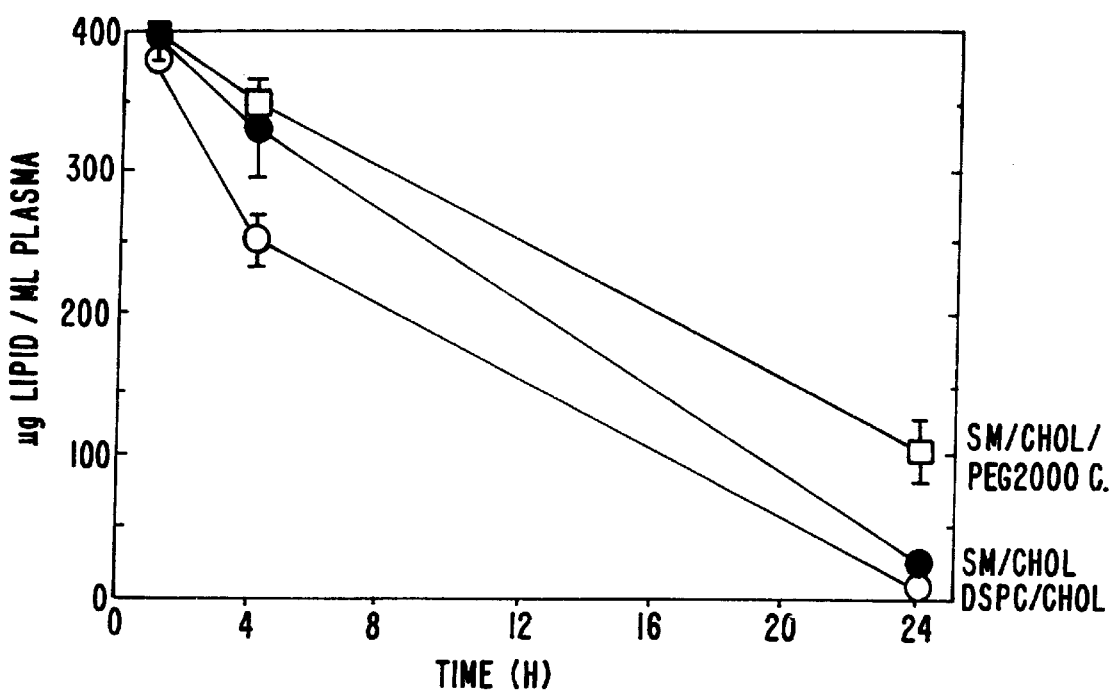

This example illustrates the plasma clearance for 100 nm liposomes prepared of DSPC/Chol (55:45 mol %; open circles), Sphingomyelin/Chol (55:45 mol %; filled circles), and Sphingomyelin/Chol/$PEG_{2000}$Ceramide (50:45:5 mol %; open squares). The results are presented in FIG. 1B. Lipid mixtures were prepared in chloroform ($CHCl_3$) and subsequently dried under a stream of nitrogen gas. The resulting lipid film was placed under high vacuum for at least 2 hours prior to hydration with a 300 mM citrate buffer (pH 4.0). Liposomes were then prepared by extrusion through 100 nm pore size filters using an Extruder preheated to 65° C. prior to extrusion. The resulting vesicles were diluted with 150 mM NaCl, 20 mM Hepes, pH 7.4 and the pH adjusted to 7.4 by titration with 500 mM sodium phosphate. The sample was then heated at 60° C. for 10 minutes. The resulting liposomes exhibited a mean diameter of approximately 120 nm. These liposomes were diluted such that mice (female BDF1) could be given an i.v. dose of lipid equivalent to 20 mg/kg in an injection volume of 200 μl. At the time points indicated in FIG. 1B, blood samples were taken by cardiac puncture. The amount of lipid in the resulting sample was determined by measuring the amount of 3[H]-cholesteryl hexadecyl ether present. This non-exchangeable, non-metabolizable lipid marker was incorporated into the liposomes prior to formation of the lipid film.

EXAMPLE 9

Vincristine Retention

In this example, vincristine retention by Sphingomyelin/ Chol (55:45 mol %) liposomes within the circulation was shown not to be affected by incorporation of PEG$_{2000}$Ceramide. In contrast, similar formulations prepared with PEG$_{2000}$-Phosphatidylethanolamine (PEG-PE) exhibit significantly reduced drug retention. The results were obtained by measuring both liposomal lipid (14[C]-cholesterylhexadecyl ether) and drug (3[H]-Vincristine) in plasma collected form BDF1 mice given an i.v. injection of liposomal vincristine (2 mg drug/kg). Samples were injected in a volume of 200 µl. The liposomes were prepared as described below.

Figure 2:
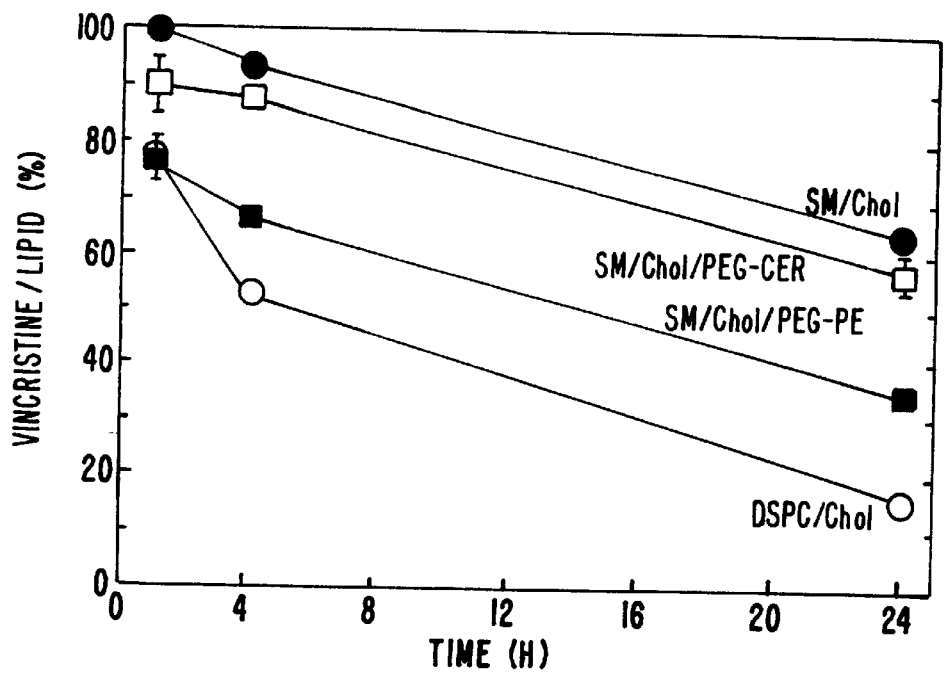
FIG. 2 graphically shows that the incorporation of PEG modified ceramide into liposomal vincristine formulations does not adversely affect drug retention characteristics. Vincristine retention by Sphingomyelin/Chol (55:45 mol %; filled circles) liposomes within the circulation is not affected by incorporation of PEG$_{2000}$Ceramide (50:45:5 mol %; open squares). Vincristine retention is also shown for DSPC/Chol (55:45 mol %; open circles) and SM/Chol/PEG-PE (Phosphatidylethanolamine) (50:45:5 mol %; filled squares).

The dry lipid was hydrated with 300 mM citrate -buffer, pH 4.0. Following extrusion, the vesicles (100 mg/ml) were added to a solution of vincristine (Oncovin; 1 mg/ml) to achieve a drug:lipid weight ratio of 0.1:1. The exterior pH of the liposome/vincristine mixture was raised to pH 7.0–7.2 by titration with 500 mM sodium phosphate and immediately the sample was heated at 60° C. for 10 minutes to achieve encapsulation of the vincristine. At the time points following i.v. administration in mice, shown in FIG. 2, blood samples were taken by cardiac puncture. The amount of vincristine and the amount of lipid were measured by use of appropriately labeled markers. The ratio of drug to lipid was then determined and plotted as a percentage of the original drug to lipid ratio. The DSPC/Chol liposome is represented by open circles, the SM/Chol liposome by filled circles; the SM/Chol/PEG$_{2000}$-ceramide by open squares; and the SM/CHOL/PEG-PE by filled squares.

EXAMPLE 10

Various PEG-Ceramide Acyl Chain Lengths and Effects on Retention Time Methods

One hundred (100) mg of total lipid was dissolved in CHCl$_3$ with 5 µCi of $^{14}$H-cholesterylhexadecyl ether (Amersham custom synthesis). Lipid preparations consisted of egg sphingomyelin (SM)/cholesterol/PEG$_{2000}$-ceramide (SM/chol/PEG-Ceramide; 55/40/5, mol/mol/mol) or of egg sphingomyelin/cholesterol/PEG$_{2000}$-distearolyphosphatidylethanolamine (SM/chol/PEG-DSPE; 55/40/5, mol/mol/mol). The PEG$_{2000}$-ceramides used in this study had fatty amide chain lengths of C8, C14, C20 or C24 or were synthesized from egg ceramide (egg-CER). Bulk CHCl$_3$ was removed under a stream of nitrogen gas, then residual solvent was removed by placing the lipid film under high vacuum overnight.

Liposomes were prepared by hydration of the lipid film with 1.0 mL of 0.3M citrate (pH 4.0) using extensive vortexing and brief heating to 65° C. (Aliquots of this suspension were removed for determination of the specific activity.) The resulting lipid suspension was freeze/thaw cycled 5 times between –196° C. and 65° C. Large unilamellar liposomes were produced by extrusion technology; the lipid suspension was passed through two stacked 0.1 µm filters at 65° C. using The Extruder (Lipex Biomembranes, Vancouver, B.C.).

As a separate operation, 2.0 mg of vincristine (as 2.0 mL of vincristine sulfate at 1.0 mg/mL; David Bull Laboratories, Mulgrave, Australia) was labelled by the addition of 5 µCi of $^3$H-vincristine (Amersham) and aliquots removed for the determination of vincristine specific activity.

For the liposomal encapsulation of vincristine, 5–6 mg of each lipid was removed to a glass test tube and labelled vincristine added to achieve a vincristine/lipid ratio of 0.1/1.0 (wt/wt). This mixture was equilibrated for 5–10 minutes at 65° C., then vincristine encapsulation was initiated by the addition of sufficient 0.5M Na$_2$HPO$_4$ to bring the solution pH to 7.0–7.5. Vincristine uptake was allowed to proceed for 10 minutes at 65° C., and the sample then cooled to room temperature and diluted with 150 mM NaCl, 20 mM Hepes (pH 7.5) (HBS) to the final concentration required for in vivo testing. The uptake of vincristine into the liposomes was determined by the centrifugation of 100 µL of liposomes on a 1.0 mL mini-column of Sephadex G-50 pre-equilibrated in HBS. The eluate was assayed for vincristine/lipid ratio by liquid scintillation counting (LSC).

Female BDF1 mice were administered i.v. by tail vein injection with liposomal vincristine at a dose of 20 mg lipid/kg, or 2 mg vincristine/kg. At 1, 4 and 24 hours after administration, blood was recovered by cardiac puncture into EDTA-containing Micro-Tainer tubes. Plasma was obtained by centrifugation at 2000 g for 15 minutes, and aliquots were assayed for lipid and vincristine content by LSC.

All data represent the means (±standard error) from 3 mice per time point, i.e., 9 animals/group. The half-lives of lipid, vincristine and the vincristine/lipid ratio were obtained from the slope of the semi-log plot of concentration vs. time. All $r^2$ values for the linear regression of these slopes were >0.98. Experiments with the C20 chain length of PEG$_{2000}$-ceramide were performed twice, and are presented separately.

Results

Figure 3:
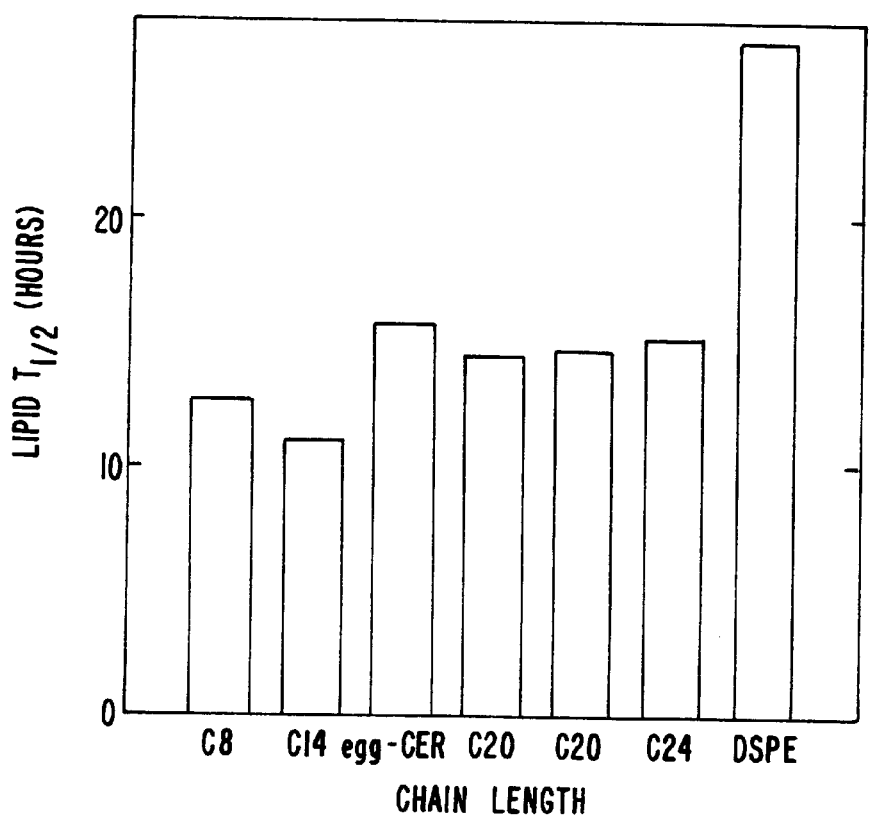
FIG. 3 shows the lipid circulation half-life ($T_{1/2}$) values (in hours) of various SM/cholesterol liposomes, including those containing PEG$_{2000}$-ceramides of various fatty amide chain lengths and those containing PEG$_{2000}$-DSPE (distearolyphosphatidylethanolamine).

The results presented in FIG. 3 (Lipid T$_{1/2}$) show that the half-life of SM/cholesterol liposomes containing 5 mol % PEG$_{2000}$-DSPE is approximately two-fold greater than SM/cholesterol liposomes containing PEG$_{2000}$-ceramides (PEG-Ceramide), regardless of the chain length. For the PEG-Ceramides, there was no significant influence of fatty acyl chain length on circulation longevity in these vincristine-loaded liposomes.

Figure 4:
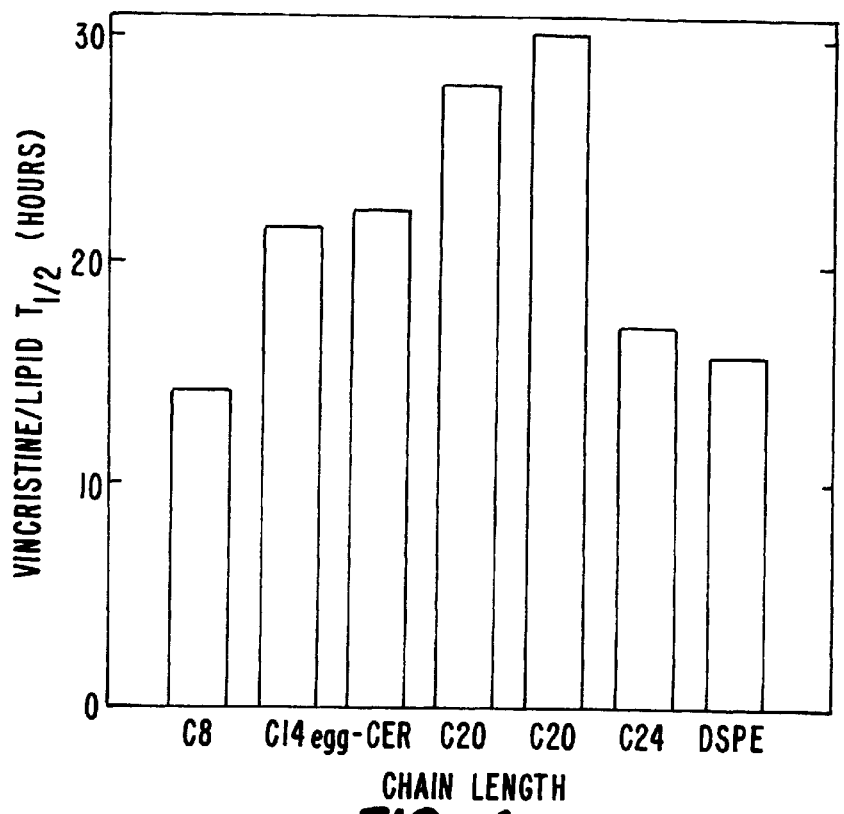
FIG. 4 illustrates the circulation half-life values ($T_{1/2}$) (in hours) of the vincristine/lipid ratios (vincristine retention) for liposomes, containing vincristine with various PEG$_{2000}$-ceramides, as well as PEG$_{2000}$-DSPE.

The results presented in FIG. 4 (vincristine/lipid T$_{1/2}$) indicate that there is a significant influence of acyl chain length on vincristine retention in the liposomes during circulation in the plasma. Specifically, C20 PEG-Ceramide was retained significantly better than both shorter (C8, C14, egg-CER and C24) chain lengths of PEG-Ceramide and also better than PEG-DSPE. The C20 chain lengths of PEG-Ceramide had half-life values for the vincristine/lipid ratio of 28–30 hours; about twice as long as those observed for the poorest vincristine retaining formulations at 15 hours (C8 PEG-Ceramide and PEG-DSPE).

Figure 5:
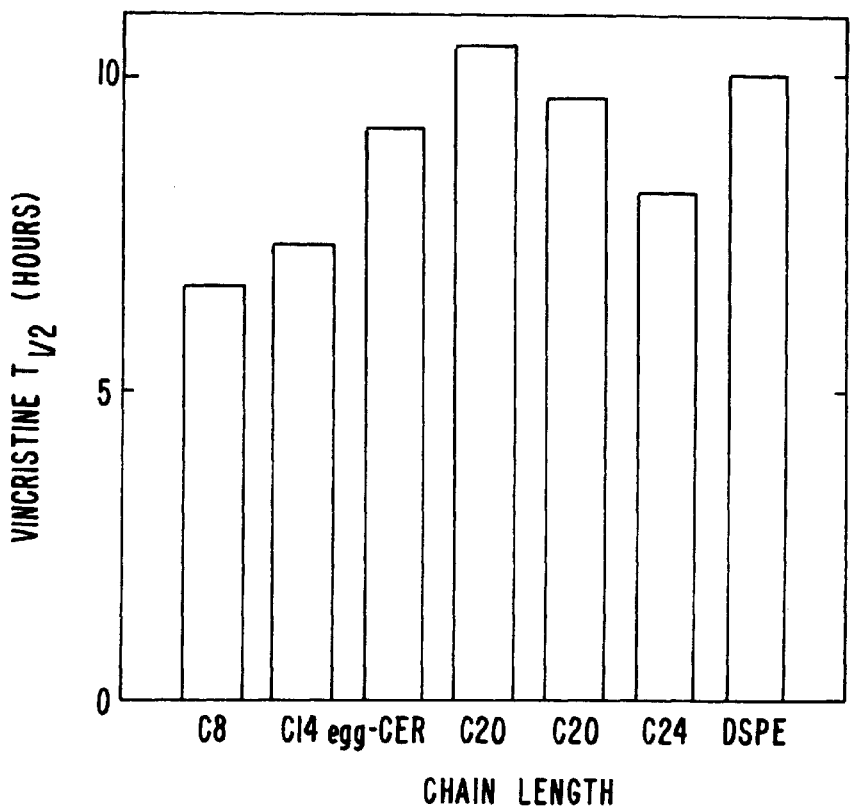
FIG. 5 presents the circulation half-life values ($T_{1/2}$) (in hours) of vincristine-containing liposomes.

The combined result of lipid circulation longevity and drug retention within these liposomes is the circulation half-lives of vincristine (see FIG. 5). Amongst the PEG-Ceramides, the C20 chain length resulted in the greatest circulation lifetime for the vincristine (9.5–10.5 hours T½ vs. 7–9 hours for the C8, C14, C24 and egg-CER chain lengths). In the samples containing PEG-DSPE, the combined influence of longer liposome circulation lifetime (FIG. 3) contrasted with poor vincristine retention (FIG. 4), resulted in overall drug half-life very similar to the C20 PEG-Ceramide.

EXAMPLE 11

Fusogenic Liposomes

The ability of amphipathic polyethyleneglycol (PEG) derivatives to stabilize fusogenic liposomes containing a cationic lipid in vivo were examined in this study. A freeze-fracture electron microscope analysis of liposomes composed of dioleoylphosphatidylethanolamine (DOPE) and N,N-dioleoyl-N,N-dimethylammonium chloride (DODAC) showed that inclusion of amphipatic PEG derivatives, PEG-DSPE and PEG-Ceramide (PEG-Ceramide) effectively prevented liposome aggregation in the presence of mouse serum. Biodistribution of fusogenic liposomes composed of DOPE and DODAC, additionally containing an amphipathic polyethyleneglycol (PEG) derivative, were then examined in mice using $^3$H-labelled cholesterylhexadecylether as a lipid marker. Amphipathic PEG derivatives included PEG-DSPE and various PEG-Ceramide (PEG-Cer) with different acyl chain length ranging from C8 to C24. DOPE/DODAC liposomes (85:15, mol/mol) were shown to be cleared rapidly from the blood and accumulate exclusively in the liver. Inclusion of amphipathic PEG derivatives at 5.0 mol % of the lipid mixture resulted in increased liposome levels remaining in the blood and concomitantly decreased accumulation in the liver. Among various amphipathic PEG derivatives, PEG-DSPE shows the highest activity in prolonging the circulation time of DOPE/DODAC liposomes. The activity of PEG-Ceramide is directly proportional to the acyl chain length: the longer the acyl chain, the higher the activity. The activity of PEG-Ceramide (C20) exhibiting the optimal acyl chain length depends on its concentration of the lipid mixture with the maximal circulation time obtained at 30 mol % of the lipid mixture. While inclusion of amphipathic PEG derivatives in the lipid composition generally results in increased circulation time of DOPE/DODAC liposomes, the presence of a cationic lipid, DODAC, appeared to promote their rapid clearance from the blood.

The preparations and uses of DODAC liposomes are disclosed in U.S. patent application Ser. No. 08/316,399, filed Sep. 30, 1994, now abandoned, the teachings of which are incorporated herein by reference.

Fusogenic liposomes incorporating bilayer stabilizing components are disclosed in U.S. patent application Ser. No. 08/316,407, filed Sep. 30, 1994, now abandoned, and U.S. patent application Ser. No. 08/485,608, filed Jun. 7, 1995 (Attorney Docket Number 016303-001310), the teachings of which are incorporated herein by reference.

MATERIALS AND METHODS

Liposome Preparation

Small unilamellar liposomes composed of DOPE and DODAC additionally containing amphipathic PEG derivatives at various ratios were prepared by the extrusion method. Briefly, the solvent-free lipid mixture containing $^3$H-labelled CHE, as a nonexchangeable and nonmetabolizable lipid marker, was hydrated with distilled water overnight. Normally, the liposome suspension (5 mg lipid per ml) was extruded, at room temperature, 10 times through stacked Nucleopore membranes (0.1 μm pore size) using an extrusion device obtained from Lipex Biomembranes, Inc. to generate liposomes with homogeneous size distributions. Liposome size was determined by quasi-elastic light scattering using a particle sizer and expressed as average diameter with standard deviation (SD).

Liposome Biodistribution Study $^3$H-labelled liposomes with various lipid compositions were injected i.v. into female CD-1 mice (8–10 weeks old) at a dose of 1.0 mg lipid per mouse in 0.2 ml of distilled water. At specified time intervals, mice were killed by overexposure to carbon dioxide, and blood was collected via cardiac puncture in 1.5-ml microcentrifuge tubes and centrifuged (12000 rpm, 2 min, 4° C.) to pellet blood cells. Major organs, including the spleen, liver, lung, heart, and kidney, were collected, weighed, and homogenized in distilled water. Fractions of the plasma and tissue homogenates were transferred to glass scintillation vials, solubilized with Solvable (NEN) at 50° C. according to the manufacturer's instructions, decolored with hydrogen peroxide, and analyzed for $^3$H radioactivity in scintillation fluid in a Beckman counter. Data were expressed as percentages of the total injected dose of $^3$H-labelled liposomes in each organ. Levels of liposomes in the plasma were determined by assuming that the plasma volume of a mouse is 5.0% of the total body weight.

RESULTS AND DISCUSSION

Freeze-Fracture Electron Microscopic Studies

Liposomes composed of DOPE/DODAC (85:15, mol/mol), DOPE/DODAC/PEG-Ceramide (C20) (80:15:5, mol/mol), and DOPE/DODAC/PEG-DSPE (80:15:5, mol/mol) were prepared by the extrusion method and had similar average diameters (100 nm). Freeze-fracture electron micrographs of the three liposomal formulations showed unilamellar liposomes with relatively narrow size ranges. However, preincubation of DOPE/DODAC liposomes in 50% mouse serum at 37° C. for 30 minutes resulted in their massive aggregations. On the other hand, both DOPE/DODAC/PEG-Ceramide (C20) and DOPE/DODAC/PEG-DSPE liposomes did not show any aggregation when these liposomes were pretreated with mouse serum. Thus, these results show the effectiveness of amphipathic PEG derivatives in preventing serum-induced rapid aggregations of DOPE/DODAC liposomes.

Biodistribution of DOPE/DODAC Liposomes Containing Amphipathic PEG Derivatives DOPE/DODAC liposomes with or without amphipathic PEG derivatives were prepared to include $^3$H-labelled cholesterol hexadecylether as a lipid marker, and their biodistribution was examined in mice at 1 hour after injection. Liposomes tested in this study were composed of DOPE/DODAC (85:15, mol/mol), DOPE/DODAC/PEG-Ceramide (80:15:5, mol/mol), and DOPE/DODAC/PEG-DSPE (80:15:5, mol/mol). To also examine the effect of the hydrophobic anchor on biodistribution of liposomes, various PEG-Ceramide derivatives with different acyl chain lengths were used. These liposomal formulations had similar average diameters, ranging from 89 to 103 nm. Table II below shows levels of liposomes in the blood, spleen, liver, lung, heart, and kidney, together with respective blood/liver ratios. DOPE/DODAC liposomes were shown to be cleared rapidly from the blood and accumulate exclusively in the liver with the blood/liver ratio of approximately 0.01. Inclusion of amphipathic PEG derivatives at 5.0 mol % in the lipid composition resulted in their increased blood levels and accordingly decreased liver accumulation to different degrees. DOPE/DODAC/PEG-DSPE liposomes showed the highest blood level (about 59%) and the lowest liver accumulation (about 35%) with the blood/liver ratio of approximately 1.7 at 1 hour after injection. Among various PEG-Ceramide derivatives with different acyl chain lengths, PEG-Ceramide (C20)-containing liposomes showed the highest blood level (about 30%) with the blood/liver ratio of approximately 0.58, while PEG-Ceramide (C8)-containing liposomes showed a lower blood level (about 6%) with the blood/liver ratio of approximately 0.1. It appeared that, among different PEG-Ceramide derivatives, the activity in increasing the blood level of liposomes is directly proportional to the acyl chain length of ceramide; the longer the acyl chain length, the greater the activity. It also appeared that the optimal derivative for increasing the blood level of liposomes is PEG-Ceramide (C20).

sition resulted in prolonged circulation times in the blood. Estimated half-lives in the α-phase for DOPE/DODAC/PEG-Ceramide (C20) (75:15:10, mol/mol) and DOPE/

TABLE II

Effect of Amphipathic PEG Derivatives on Biodistribution of DOPE/DODAC Liposomes

| PEG-Derivative | Average Diameter (mm) | % injected dose | | | | | | | |
|---|---|---|---|---|---|---|---|---|---|
| | | Blood | Liver | Spleen | Lung | Heart | Kidney | Total | Blood/Liver |
| None | 103 (29) | 0.8 (0.4) | 64.4 (2.) | 3.1 (1.8) | 1.2 (0.2) | 0.2 (0.0) | 0.3 (0.0) | 70.0 (1.4) | 0.012 |
| PEG DSPE | 95 (26) | 59.1 (8.2) | 34.7 (2.1) | 2.9 (0.1) | 1.9 (0.8) | 1.7 (0.4) | 1.2 (0.5) | 101.4 (6.1) | 1.703 |
| PEG-Cer (C8) | 89 (24) | 6.5 (1.9) | 62.8 (3.4) | 4.2 (1.0) | 0.5 (0.3) | 0.3 (0.1) | 0.3 (0.1) | 74.6 (5.1) | 0.104 |
| PEG-Cer (C14) | 93 (25) | 5.9 (0.5) | 55.9 (1.0) | 3.3 (0.2) | 0.1 (0.0) | 0.1 (0.0) | 0.1 (0.0) | 65.4 (1.6) | 0.106 |
| PEG-Cer (C16) | 93 (24) | 13.9 (2.1) | 57.5 (2.0) | 2.6 (0.1) | 0.0 (0.0) | 0.2 (0.1) | 0.0 (0.0) | 74.3 (4.0) | 0.242 |
| PEG-Cer (C20) | 101 (24) | 29.8 (4.8) | 51.0 (2.2) | 1.9 (0.2) | 0.0 (0.0) | 0.3 (0.1) | 0.0 (0.0) | 82.8 (2.8) | 0.584 |
| PEG-Cer (C24) | 92 (28) | 26.7 (0.8) | 46.7 (7.6) | 5.7 (1.2) | 1.0 (0.2) | 0.9 (0.2) | 0.4 (0.1) | 81.5 (4.1) | 0.572 |

$^3$H-labelled liposomes composed of DOPE/DODAC (75:15, mol/mol) additionally containing an indicated PEG derivative at 5.0 mol % of the lipid mixture were injected i.v. into mice. Biodistribution was examined at 1 h after injection and expressed as percentage of injected dose of liposomes with SD (n = 3).

Optimizations of DOPE/DODAC Liposomes for Prolonged Circulation Times

Figure 6:
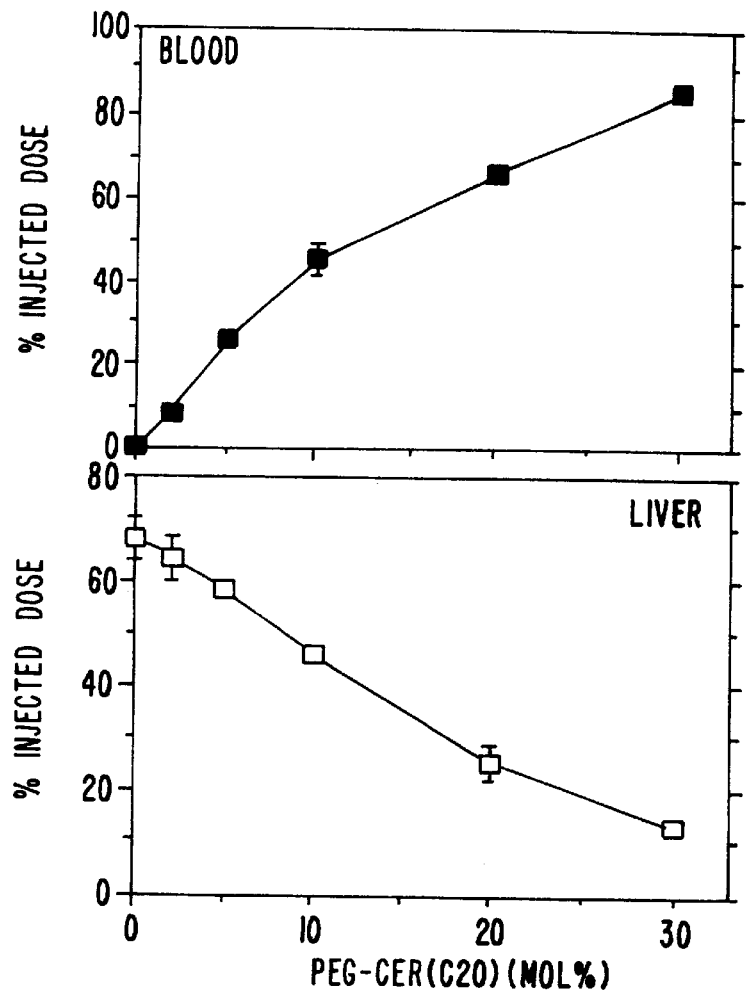
FIG. 6 graphically shows the effect of increasing concentrations of PEG-Ceramide (C20) on biodistribution of liposomes in the blood and liver. $^3$H-labeled liposomes composed of DOPE (dioleoylphosphatidylethanolamine), 15 mol % DODAC (N,N-dioleoyl-N,N-dimethylammonium chloride) and the indicated concentrations of PEG-Ceramide (C20) were injected i.v. into mice. Biodistribution was examined at 1 hour after injection, and the data were expressed as a percentage of the injected dose in the blood (upper panel) and liver (lower panel) with SD (standard deviation) (n=3).

The effect of increasing concentrations of PEG-Ceramide (C20) in the lipid composition on biodistribution of DOPE/DODAC liposomes was examined. PEG-Ceramide (C20) was included in DOPE/DODAC liposomes at increasing concentrations (0–30 mol %) in the lipid composition, while the concentration of DODAC was kept at 15 mol % of the lipid mixture. Liposomes were prepared by the extrusion method and had similar average diameters ranging from 102 nm to 114 nm. Liposomes were injected i.v. into mice, and biodistribution was examined at 1 hour after injections. FIG. 6 shows the liposome level in the blood and liver at 1 hour after injections as a function of the PEG-Ceramide (C20) concentration. Clearly, increasing the concentration of PEG-Ceramide in the lipid composition resulted in progressive increase in liposome levels in the blood, accompanied by decreased accumulation in the liver. The highest blood level (about 84% at 1 hour after injection) was obtained for DOPE/DODAC/PEG-Ceramide (C20) (55:15:30, mol/mol) showing the blood/liver ratio of about 6.5.

Figure 7:
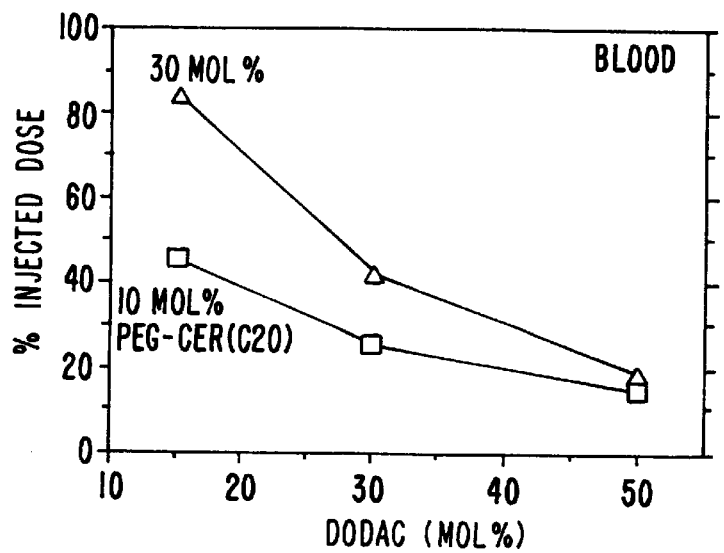
FIG. 7 graphically illustrates the effect of increasing concentrations of DODAC on the biodistribution of liposomes in the blood. $^3$H-labeled liposomes composed of DOPE, 10 (open squares) or 30 (open triangles) mol % PEG-Ceramide (C20), and the indicated concentration of DODAC were injected i.v. into mice. Biodistribution was examined at 1 hour after injection, and the data were expressed as a percentage of the injected dose in the blood with SD (n=3).

The effect of increasing concentrations of DODAC on the biodistribution of DOPE/DODAC liposomes also was examined. DOPE/DODAC liposomes containing either 10 mol % or 30 mol % PEG-Ceramide (C20) and various concentrations (15, 30, 50 mol %) were prepared by the extrusion method and had similar average diameters ranging from 103 to 114 nm. Biodistribution was examined at 1 hour after injections, and expressed as percentages of liposomes in the blood as a function of the DODAC concentration (FIG. 7). As shown in FIG. 7, increasing DODAC concentrations in the lipid composition resulted in decreased levels in the blood for both liposomal formulations. Thus, the presence of a cationic lipid, DODAC, in the lipid composition results in rapid clearance from the blood. Also, shown in FIG. 7 is that such a DODAC effect can be reversed by increasing the concentration of PEG-Ceramide (C20) in the lipid composition.

Figure 8:
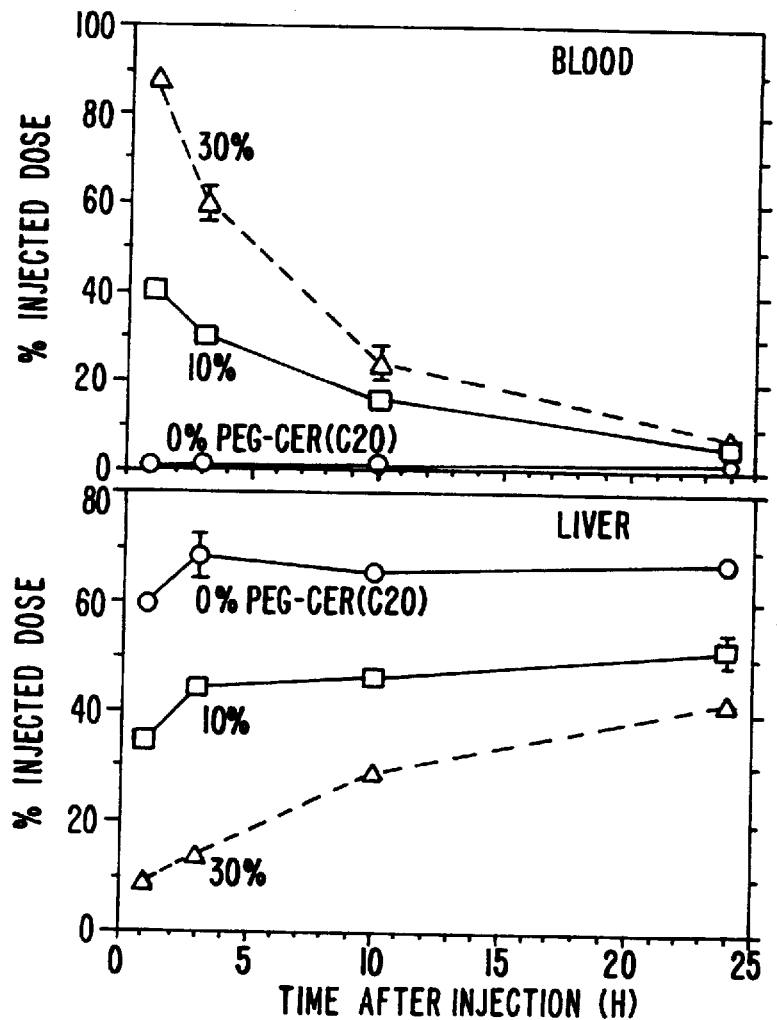
FIG. 8 graphically shows the liposome levels in the blood and liver at different times after injection. $^3$H-labeled liposomes composed of DOPE/DODAC (85:15 mol/mol) (open circles with 0% PEG-Ceramide (C20)), DOPE/DODAC/PEG-Ceramide (C20) (75:15:10 mol/mol/mol) (open squares with 10% PEG-Ceramide (C20)), and DOPE/DODAC/PEG-Ceramide (C20) (55:15:30 mol/mol/mol) (open triangles with 30% PEG-Ceramide (C20)) were injected i.v. into mice. Biodistribution was examined at indicated times, and the data were expressed as a percentage of the injected dose in the blood (upper panel) and in the liver (lower panel) with SD (n=3).

FIG. 8 shows time-dependent clearances of DOPE/DODAC liposomes with or without PEG-Ceramide from the blood. Only a small fraction of injected DOPE/DODAC liposomes remained in the blood, while increasing the concentration of PEG-Ceramide (C20) in the lipid composition resulted in prolonged circulation times in the blood. Estimated half-lives in the α-phase for DOPE/DODAC/PEG-Ceramide (C20) (75:15:10, mol/mol) and DOPE/DODAC/PEG-Ceramide (C20) (55:15:30, mol/mol) were <1 hour and 5 hours, respectively.

CONCLUSIONS

The above studies indicate that there are several levels at which biodistribution of fusogenic liposomes containing a cationic lipid can be controlled by inclusion of amphipathic PEG derivatives. Data in Table II shows that the hydrophobic anchor of amphipathic PEG derivatives has an important role in determining biodistribution of DOPE/DODAC liposomes. Studies using various PEG-Ceramide derivatives with different acyl chain lengths showed that the longer the acyl chain length of PEG-Ceramide, the greater the activity in prolonging the circulation time of DOPE/DODAC liposomes. These results are consistent with the rate at which amphipathic PEG derivatives dissociate from the liposome membrane is directly proportional to the size of the hydrophobic anchor. Accordingly, PEG-Ceramide derivatives with a longer acyl chain can have stronger interactions with other acyl chains in the liposome membrane and exhibit a reduced rate of dissociation from the liposome membrane, resulting in stabilization of DOPE/DODAC liposomes for a prolonged period of time and thus their prolonged circulation time in the blood.

In addition to the hydrophobic anchor of amphipathic PEG derivatives, the concentration of amphipathic PEG derivatives in the lipid membrane can also be used to control in vivo behavior of DOPE/DODAC liposomes. Data in FIG. 6 show that increasing the concentration of PEG-Ceramide (C20) in the lipid composition resulted in increased liposome levels in the blood. The optimal concentration of PEG-Ceramide (C20) in the lipid composition was found to be 30 mol % of the lipid mixture. It appeared that the circulation time of DOPE/DODAC/PEG-Ceramide (C20) liposomes is determined by the relative concentrations of two lipid compositions, DOPE and PEG-Ceramide, exhibiting opposite effects on liposome biodistribution. While amphipathic PEG derivatives show the activity in prolonging the circulation time of liposomes in -the blood, a cationic lipid, DODAC, shows the activity to facilitate liposome clearance from the blood. Thus, for the maximal circulation time in the blood, an appropriate concentration of amphipathic PEG derivatives and a minimal concentration of DODAC should be used. It should be noted, however, that an optimal liposome formulation for the prolonged circulation time in the blood is not necessarily the one suitable for an intended application in delivery of certain therapeutic agents. Both pharmacokinetic and pharmacodynamic aspects of fusogenic liposomes should be examined for different applications using different therapeutic agents.

All publications and other references or patent documents herein are incorporated by reference. It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which the claims are entitled.

What is claimed is:

1. A lipid compound of the formula

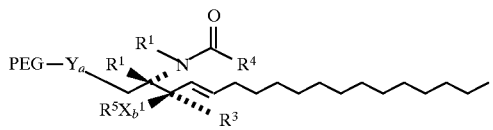

Formula I wherein:
$R^1$, $R^2$, and $R^3$ are independently hydrogen, $C_1$–$C_6$ alkyl, acyl, or aryl;
$R^4$ is hydrogen, $C_1$–$C_{30}$ alkyl, $C_2$–$C_{30}$ alkenyl, $C_2$–$C_{30}$ alkynyl, or aryl;
$R^5$ is hydrogen, alkyl, acyl, aryl, or PEG;
$X^1$ is —O—, —S—, or —$NR^6$—, where $R^6$ is hydrogen, $C_1$–$C_6$ alkyl, acyl or aryl; or when $R^5$ is PEG and b is 1, $X^1$ is also —$Y^1$-alk-$Y^2$;
Y is —$NR^7$—, where $R^7$ is hydrogen, $C_1$–$C_6$ alkyl, acyl or aryl, or Y is —O—, —S— or —$Y^1$-alk-$Y^2$—, wherein $Y^1$ and $Y^2$ are independently amino, amido, carboxyl, carbamate, carbonyl, carbonate, urea, or phosphoro; and alk is $C_1$–$C_6$ alkylene;
PEG is a polyethylene glycol with an average molecular weight from about 550 to about 8,500 daltons optionally substituted by $C_1$–$C_3$ alkyl, alkoxy, acyl or aryl;
wherein a is 0 or 1; and b is 1 unless $R^5$ is PEG wherein b is 0 or 1.

2. The lipid of claim 1, wherein $R^1$, $R^2$, $R^3$, and $R^5$ are hydrogen; $R^4$ is alkyl; $X^1$ is O; Y is succinate; and PEG has an average molecular weight of about 2,000 to about 5,000 daltons and is substituted with methyl at the terminal hydroxyl position.

3. The lipid of claim 1, wherein $R^1$, $R^2$, $R^3$, and $R^5$ are hydrogen, $R^4$ is alkyl; $X^1$ is O; Y is —NH—; and PEG has an average molecular weight of about 2,000 to about 5,000 daltons and is substituted with methyl at the terminal hydroxyl position.

4. A liposome comprising the lipid of claim 1.

5. The liposome of claim 4 further comprises one or more bioactive agents.

6. A method of delivering a bioactive agent to cells comprising encapsulating the agent in a liposome of claim 4 to form a liposome-bioactive complex and contacting the cells with the complex.

7. The method of claim 6 wherein the bioactive agent is selected from the group consisting of antitumor agents, antibiotics, immunomodulators, anti-inflammatory drugs and drugs acting on the central nervous system.

8. The method of claim 6 wherein the bioactive agent is a protein or a peptide.

9. A method of treating a disease in a patient comprising administering to the patient a therapeutically effective amount of a pharmaceutical composition containing one or more bioactive agents encapsulated in a liposome of claim 4.

10. A method for delivering a vaccine to a patient comprising encapsulating a bioactive agent for a vaccine in a liposome of claim 4 to form a liposome-coated vaccine and administering the liposome-coated vaccine to the patient.

11. A method of immunizing a patient comprising encapsulating an antigen in a liposome of claim 4 to form a liposome-encapsulated antigen and administering the liposome-encapsulated antigen to the patient.

12. A pharmaceutical formulation comprising the liposome of claim 5 and a physiologically-acceptable adjuvant thereof.

13. The formulation of claim 1, wherein the bioactive agent is vincristine.

14. A kit for labeling liposome of claim 5, comprising a container with at least two compartments wherein the first compartment comprises materials for preparing a label and the second compartment comprises the liposome of claim 5.

15. A lipid complex comprising the lipid of claim 1.

16. The liposome of claim 5 comprising a gene construct for therapeutic use.

17. The liposome of claim 5 comprising an oligonucleotide for therapeutic use.

18. The lipid of claim 1, wherein $R^1$, $R^2$, $R^3$ and $R^5$ are hydrogen; $R^4$ is $C_7$–$C_{23}$ alkyl; $X^1$ is O; Y is succinate; and PEG has an average molecular weight of about 2,000 Daltons, and is substituted with monomethoxy.

19. The lipid of claim 18, wherein $R^4$ is $C_{13}$–$C_{19}$ alkyl.

20. The lipid of claim 19, wherein $R^4$ is $C_{19}$ alkyl.

21. The lipid of claim 19, wherein $R^4$ is $C_{13}$ alkyl.

22. A liposome comprising the lipid of claim 18.

23. The liposome of claim 22 further comprises one or more bioactive agents.

24. A liposome comprising a lipid compound of the formula

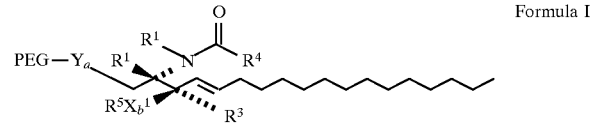

Formula I wherein:
$R^1$, $R^2$, $R^3$ and $R^5$ are hydrogen;
$R^4$ is $C_7$–$C_{23}$ alkyl;
$X^1$ is O;
Y is succinate; and
PEG has an average molecular weight of about 2,000 Daltons, and is substituted with monomethoxy;
said liposome further comprising DOPE, DODAC and one or more bioactive agents.

25. The liposome of claim 24, wherein mole percent ratio of the lipid is about 0.01 to about 60.

26. The liposome of claim 25, wherein $R^4$ is $C_{13}$–$C_{19}$ alkyl.

27. A method of delivering a bioactive agent to cells comprising encapsulating the agent in a liposome to form a liposome-bioactive complex, said liposome comprising a lipid compound of the formula

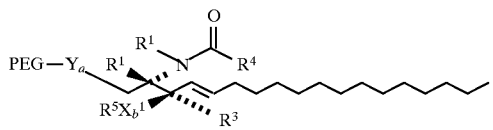

Formula I wherein:

$R^1$, $R^2$, $R^3$ and $R^5$ are hydrogen;

$R^4$ is $C_7$–$C_{23}$ alkyl;

$X^1$ is O;

Y is succinate; and

PEG has an average molecular weight of about 2,000 Daltons, and is substituted with monomethoxy; and contacting the cells with the liposome-bioactive complex.

28. The method of claim 27, wherein $R^4$ is $C_{13}$–$C_{19}$ alkyl.

29. The method of claim 28, wherein the liposome additionally comprises DOPE and DODAC.

30. A pharmaceutical formulation comprising the liposome of claim 22 and a physiologically-acceptable adjuvant therefor.

* * * * *

UNITED STATES PATENT AND TRADEMARK OFFICE
CERTIFICATE OF CORRECTION

PATENT NO.   : 5,820,873
DATED        : October 13, 1998
INVENTOR(S)  : Choi et al.

It is certified that error appears in the above-identified patent and that said Letters Patent is hereby corrected as shown below:

Column 2,
Line 30, please replace Formula I with --

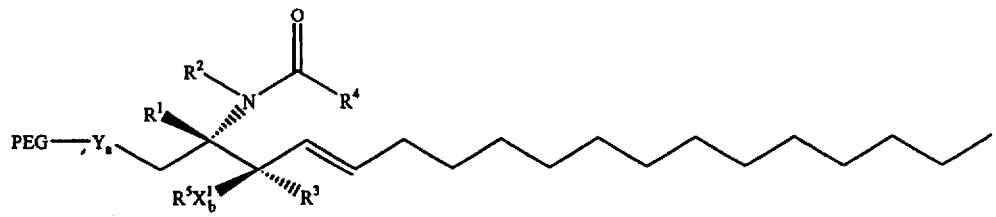

--

Column 27,
Line 20, please replace Formula I with --

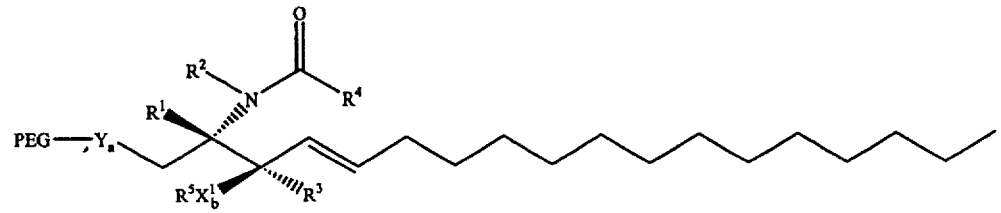

--

Column 28,
Line 45, please replace Formula I with --

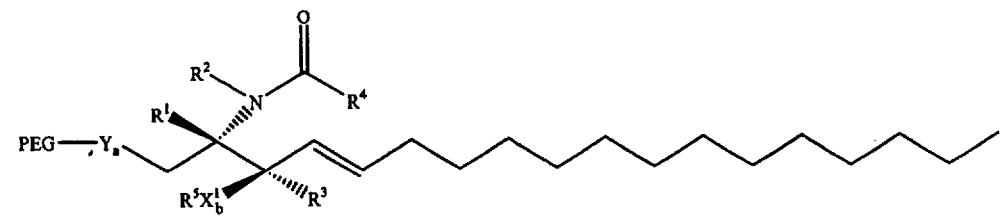

--

UNITED STATES PATENT AND TRADEMARK OFFICE
CERTIFICATE OF CORRECTION

PATENT NO. : 5,820,873
DATED : October 13, 1998
INVENTOR(S) : Choi et al.

It is certified that error appears in the above-identified patent and that said Letters Patent is hereby corrected as shown below:

Column 29,
Line 5, please replace Formula I with --

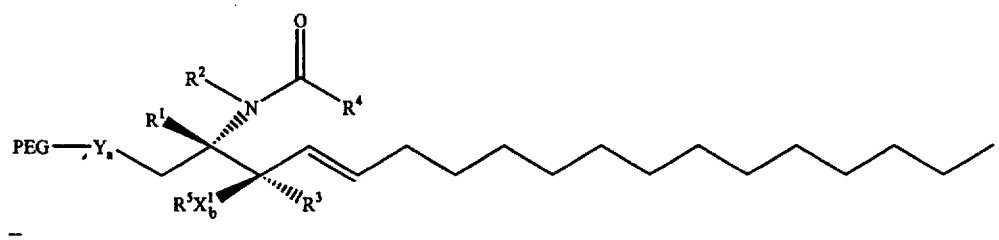

--

Signed and Sealed this

Fifth Day of February, 2002

Attest:

JAMES E. ROGAN
*Director of the United States Patent and Trademark Office*

*Attesting Officer*